US010054600B2

(12) United States Patent
Chojkier et al.

(10) Patent No.: US 10,054,600 B2
(45) Date of Patent: Aug. 21, 2018

(54) BIOMARKER COMPOSITE TEST FOR HEPATIC VEIN PRESSURE GRADIENT AND CIRRHOSIS TREATMENT

(71) Applicant: THE REGENTS OF THE UNIVERSITY OF CALIFORNIA, Oakland, CA (US)

(72) Inventors: Mario Chojkier, Delmar, CA (US); Martina Buck, Delmar, CA (US)

(73) Assignee: The Regents of the University of California, Oakland, CA (US)

( * ) Notice: Subject to any disclaimer, the term of this patent is extended or adjusted under 35 U.S.C. 154(b) by 43 days.

(21) Appl. No.: 14/892,587

(22) PCT Filed: May 22, 2014

(86) PCT No.: PCT/US2014/039172
§ 371 (c)(1),
(2) Date: Nov. 20, 2015

(87) PCT Pub. No.: WO2014/190170
PCT Pub. Date: Nov. 27, 2014

(65) Prior Publication Data
US 2016/0084849 A1    Mar. 24, 2016

Related U.S. Application Data

(60) Provisional application No. 61/826,140, filed on May 22, 2013.

(51) Int. Cl.
*G01N 33/53* (2006.01)
*G01N 33/68* (2006.01)

(52) U.S. Cl.
CPC ..... *G01N 33/6893* (2013.01); *G01N 2800/06* (2013.01); *G01N 2800/085* (2013.01); *G01N 2800/52* (2013.01); *G01N 2800/56* (2013.01); *G01N 2800/60* (2013.01)

(58) Field of Classification Search
CPC ................................................ G01N 33/6893
See application file for complete search history.

(56) References Cited

FOREIGN PATENT DOCUMENTS

| CA | 2537668 A1 | 4/2005 |
| EP | 2059817 B1 | 11/2010 |

OTHER PUBLICATIONS

Lapalus et al. Endoscopy. Jan. 2006;38(1):36-41, Abstract only, PubMed database [online], Bethesda (MD):NCBI (US) [retrieved on Jun. 22, 2017]. Retrieved from the Internet:<URL:https://www.ncbi.nlm.nih.gov/pubmed/?term=16429353>.*
International Search Report in related PCT Application No. PCT/US2014/039172, dated Oct. 14, 2014.
Buck, M. et al., "Novel Inflammatory Biomarkers of Portal Pressure in Compensated Cirrhosis Patients," Hepatology, Mar. 2014, vol. 59, No. 3, pp. 1052-1059.
Diaz-Sanchez, A., et al., "Serum Levels of Soluble Vascular Cell Adhesion Molecule in Patients with Hepatocellular Carcinoma and its Association with Severity of Liver Disease," Annals of Hepatology, Mar.-Apr. 2013, vol. 12, No. 2, pp. 236-247.
Garcia-Tsao, G., et al., "Prevention and Management of Gastroesophageal Varices and Variceal Hemorrhage in Cirrhosis," Hepatology 2007, vol. 46, No. 3, pp. 922-938.
Kropf, J. et al., "Logistic-Regression Model for Assessing Portal Hypertension by Measuring Hyaluronic Acid (Hyaluronan) and Laminin in Serum," Clinical Chemistry 1991, vol. 37, No. 1, pp. 30-35.
Vizzutti, F. et al., "Liver Stiffness Measurement Predicts Severe Portal Hypertension in Parients with HCV-Related Cirrhosis," Hepatology 2007, vol. 45, No. 5, pp. 1290-1297.

* cited by examiner

*Primary Examiner* — Prema M Mertz
(74) *Attorney, Agent, or Firm* — Eversheds Sutherland (US) LLP

(57) ABSTRACT

Diagnostic biomarker panel, method, kit, and device for diagnosing the severity and/or prognosis of cirrhosis are provided. More specifically, the invention provides a novel biomarker panel correlating to HVPG and esophageal varices. The invention further provides a biomarker panel and non-invasive test methods that predict non-clinically significant portal hypertension HVPG and non-clinically significant esophageal varices when the expression of the biomarker panel correlates with HVPG of less than 12 mmHg. The invention further provides that the patients with the expression of the biomarker panel correlating to non-clinically significant HVPG and esophageal varices can be excluded from undergoing esophagogastroduodenoscopy (EGD) screening and those correlating to HVPG equal to or greater than 12 mmHg are indicated for EGD.

10 Claims, 1 Drawing Sheet

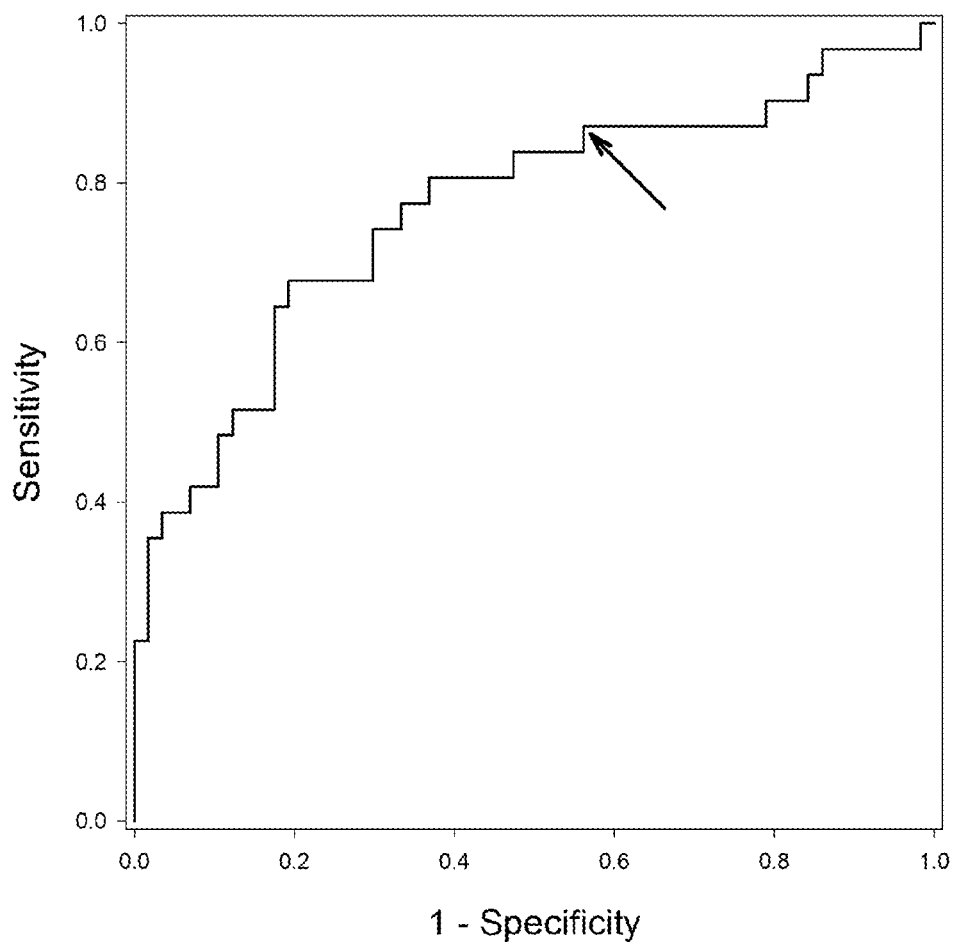

BIOMARKER COMPOSITE TEST FOR HEPATIC VEIN PRESSURE GRADIENT AND CIRRHOSIS TREATMENT

CROSS-REFERENCE TO RELATED APPLICATIONS

This application is a US National Stage of International Application No. PCT/US2014/039172, filed 22 May 2014, which claims the benefit of U.S. Provisional Application No. 61/826,140, filed 22 May 2013, the entire content of which is fully incorporated by reference herein.

STATEMENT OF GOVERNMENT INTEREST

This invention was made with government support under grant Nos. DK038652 and DK046071 awarded by National Institutes of Health (NIH). The government has certain rights in the invention.

FIELD OF THE INVENTION

The invention relates generally to the field of diagnosis and prognosis of cirrhosis and its associated complications. More specifically, the invention relates to a composite of biomarkers correlating to the hepatic vein pressure gradient (HVPG), wherein such biomarkers can also exclude or indicate the presence of clinically significant esophageal varices.

BACKGROUND OF THE INVENTION

The majority of patients who succumb to cirrhosis die due to complications of increased portal venous pressure, such as variceal hemorrhage, ascites, hepatic encephalopathy, hepatopulmonary syndrome, or hepatorenal syndrome (1; 2). The hepatic vein pressure gradient (HVPG), an indirect measure of portal pressure (3), is a prognostic indicator for long term survival in cirrhosis (1; 2). Furthermore, the HVPG can reflect progression of disease in the pre-cirrhotic stage. There is an association between the severity of the hepatic inflammation and fibrosis and the HVPG even before cirrhosis develops (4). In addition, HVPG predicts the response to hepatitis C treatment among patients with cirrhosis (5).

One of the most frequent severe complications of portal hypertension is hemorrhage from gastroesophageal varices (GEV), which is a significant cause of death in patients with cirrhosis. Reduction of the HVPG below 12 mm Hg (normal is 0-5 mm Hg), either through spontaneous reversion after the insult is resolved or with medical, radiological, or surgical interventions, effectively prevents recurrent bleeding (3; 6; 7; 8). Currently, there is no established non-invasive test to predict the portal pressure among patients who are treated medically, and thus, there is no way to predict either the response to standard of care (SOC) or the complications of portal hypertension (including potentially lethal esophageal bleeding) other than performing screening esophagogastroduodenoscopy (EGD) with the added costs and morbidity of the procedure. Although transient elastography has a very good predictive value for clinically-significant portal hypertension, there are some limitations of this technique in patients with chronic liver diseases and with obesity (9).

The ability to predict portal pressure with a simple blood test would revolutionize clinical management of patients with chronic liver diseases, as well as aid in the design and performance of clinical research into the complications of cirrhosis (1; 2). Given that liver inflammation due to liver injury and/or bacterial translocation occurs in liver cirrhosis with portal hypertension (10; 11; 12; 13; 14; 15), it would be desirable to develop a non-invasive test to predict the presence of severe portal hypertension at levels associated with the presence of variceal bleeding (2), as well as to exclude clinically significant esophageal varices so as to avoid and/or prevent the cirrhosis patients from undergoing unnecessary EGD screening.

SUMMARY OF THE INVENTION

This invention provides a non-invasive test and method to predict portal pressure in cirrhotic patients, which is a critical predictor of complications associated with the presence of variceal bleeding and ascites. More specifically, the invention provides a novel biomarker panel and assay that can be used to develop a predictive paradigm for hepatic vein pressure gradient (HVPG), the prognostic indicator for long term survival in cirrhosis, as well as esophageal varices reflecting progression of disease stage. The invention, therefore, provides methods of treating cirrhosis based on composite biomarker determination of probable HVPG and indications of whether or not to perform EGD screening.

In certain embodiments, the invention provides a biomarker panel correlating with hepatic vein pressure gradient (HVPG) measurement of portal pressure, as well as esophageal varices, as indicators for an immediate EGD procedure and long term survival in and/or prognosis of cirrhosis. The novel biomarker panel comprises two or more isolated reagents capable of detecting inflammatory biomarkers, including but not limited to: IL-1β, IL-1Rα, Fas-R, VCAM-1, TNF-β, and HSP-70, as well as biomarkers including but not limited to IL-18, toll-like receptor, such as TLR9, lymphotoxin-β, glutamine and glutamine synthase, and other heat shock proteins, such as, HSP-27, HSP-60, HSP-110, and grp170, and hyaluronan, homeocysteine, and angiotensin-II. In certain embodiments, the invention provides that at least two, at least three, at least four, at least five, and at least six of these biomarkers are combined in a composite panel to show significant correlation with HVPG as an indicator for the treatment of cirrhosis.

In other embodiments, the invention provides that presence or expression of at least six specific inflammatory biomarkers are selected including IL-1β, IL-1Rα, Fas-R, VCAM-1, TNF-β, and HSP-70 that correlate with HVPG measurements, as well as esophageal varices. In certain embodiments, the invention provides that the presence or expression of these inflammatory biomarkers correlate with HVPG of less than 12 mmHg suggest non-clinically significant HVPG, as well as non-clinically significant esophageal varices (<5 mm) and no indication for an EGD procedure. The detection of the significant correlations between the six inflammatory biomarkers: IL-1β, IL-1Rα, Fas-R, VCAM-1, TNF-β, and HSP-70 provides at least 86% accuracy excluding HVPG equal to or greater than 12 mmHg.

In other embodiments, the invention provides that the presence or expression of these inflammatory biomarkers correlating with HVPG of equal to or greater than 12 mmHg correlates with clinically significant HVPG, as well as clinically significant esophageal varices (>5 mm). Patients with expression of these inflammatory biomarkers correlating with HVPG of equal to or greater than 12 mmHg are indicated for undergoing esophagogastroduodenoscopy (EGD) screening.

The invention further provides that the non-invasive biomarker test correlates to and can be used in conjunction with established demographic and clinical laboratory parameters associated with liver diseases and/or cirrhosis, including but not limited to, age, model for end-stage liver diseases (MELD), Child-Pugh Score (CPS), platelets, alanine aminotransferase (ALT), aspartate aminotransferase (AST), and at-risk alcohol use.

The invention further provides a method for predicting HVPG and esophageal varices as a prognostic indicator for a cirrhosis patient, comprising: a) obtaining a biological sample of a patient, b) detecting expression levels of two or more inflammatory biomarkers in the sample, including but not limited to, IL-1β, IL-1Rα, Fas-R, VCAM-1, TNF-β, and HSP-70, c) correlating the expression levels of said biomarker panel with a threshold HVPG measurement, and d) diagnosing said patient with non-clinically significant HVPG and esophageal varices, when the presence or the expression levels of said biomarker panel correlates to HVPG of less than 12 mmHg. In certain embodiments, the biological sample refers to a biological fluid selected from the group consisting of whole blood, plasma, serum, or specific serum bacterial DNA. The inventive method of treating cirrhosis and detecting the biomarkers correlating to HVPG and esophageal varices can be used in conjunction with demographic and clinical laboratory parameters discussed above.

A kit and/or a device for diagnosing, prognosing, and predicting HVPG and esophageal varices as an indicator for treatment of cirrhosis is also provided. The kit comprises: a) a detection system comprising one or more detectors and reagents specific for detecting a presence or an expression levels of a biomarker panel comprising two or more biomarkers, including but not limited to, IL-1β, IL-1Rα, Fas-R, VCAM-1, TNF-β, and HSP-70, in a biological sample of said cirrhosis patient, and b) instructions for using the kit for predicting the patient with non-clinically significant HVPG or esophageal varices, when the presence or expression of said biomarker panel correlates with HVPG equal to, greater than, or less than 12 mmHg threshold.

BRIEF DESCRIPTION OF THE DRAWINGS

FIG. 1 illustrates ROC Curve for the Composite Test. An ROC curve was produced for the composite (area 0.767+/−0.057; asymptotic sigma P<0.0001; 95% CI 0.656 to 0.879). A scatter plot was drawn and a cut-point (CAT12; arrow) selected where probability of HVPG equal or >12 based on a natural break in the scatter plot. CAT12 groups were compared to actual HVPG<12. The composite test was statistically significant using several Chi-Square tests (Pearson Chi-Square P=0.017; Fisher's Exact Test P=0.025; Likelihood Ratio P=0.013; Linear-by-Linear Association P=0.018).

DETAILED DESCRIPTION OF THE INVENTION

The invention provides a biomarker assay for correlating patient hepatic vein pressure gradient (HVPG) to treat cirrhosis, comprising: combining a biological sample from a patient with a biomarker panel detecting a corresponding two or more biomarkers in the sample selected from the group consisting of IL-1β, IL-1Rα, Fas-R, VCAM-1, TNF-β, HSP-70, IL-18, TLR9, lymphotoxin-β, glutamine, glutamine synthase, HSP-27, HSP-60, HSP-110, grp170, hyaluronan, homeocysteine, and angiotensin-II. The assay further comprises detecting the expression levels of the two or more biomarkers; correlating the levels of the two or more biomarkers with a threshold HVPG, and indicating esophagogastricduodenoscopy (EGD) for the patient when the biomarker expression levels correlate to HVPG equal to or greater than 12 mmHg, or indicating no EGD for the patient when the biomarker expression levels correlate to HVPG less than 12 mmHg.

The invention provides an assay, wherein said biological sample is a biological fluid selected from the group consisting of whole blood, plasma, serum, or specific serum bacterial DNA.

The invention provides an assay, wherein said biomarker panel comprises detecting at least six biomarkers selected from the group consisting of IL-1β, IL-1Rα, Fas-R, VCAM-1, TNF-β and HSP-70.

As used herein, a "biomarker panel" refers to a composite set of selected relevant biomarkers, which can be identified by one or more well-known or later developed reagents or assays, and be performed using one or more separate containers or substrates, including but not limited to reagents involving multiplex peptide magnetic bead-based detection systems, nucleic acid hybridization, and enzyme-linked immunoassays, and proteomics techniques such as two-dimensional gel electrophoresis and mass spectrometry.

Various mathematical approaches for correlating biomarker panel results with a clinical diagnosis, prognosis or indication for further treatment, are well-known in the art. Certain methods of correlating the data are presented in the examples herein. Furthermore, biomarker panels can rely on statistical analysis known as multivariate classification or supervised learning. Exemplary methods, such as a Pearson's correlation coefficient, multiple linear regression analysis, threshold-based methods, logistic regression analysis, tree-based methods, and Support Vector Machine (SVM), can be applied to correlate biomarker panels with a clinical diagnosis, prognosis or indication for further treatment. Generalized additive models also allow one to combine data with patient clinical information to predict an outcome. Furthermore, several other methods, e.g., a Bayesian network on gene expression microarray data, perform well in proteomics based biomarker detection. Additional well-known data pre-processing and data normalization steps can be implemented. Additional computational methods and randomization techniques, such as a permutation test, cross-validation and bootstrapping, can help to evaluate and validate the performance and correlation. A more detailed discussion of methods for defining, classifying and performance validation of a biomarker panel are described in Robin et al., 2009, Expert Review of Proteomics 6 (6) p. 675-689, the entire contents of which is incorporated by reference herein.

In one aspect, the invention provides an assay, wherein said assay is further correlated with demographic and clinical laboratory parameters selected from the group consisting of age, model for end-stage liver diseases (MELD), Child-Pugh Score (CPS), platelets, alanine aminotransferase (ALT), aspartate aminotransferase (AST), and at-risk alcohol use for indicating EGD to the patient, or not indicating EGD for the patient.

The invention provides an assay, wherein the correlating with HVPG provides at least 86% accuracy excluding HVPG equal to or greater than 12 mmHg.

The invention provides a biomarker panel, wherein the biomarker panel further correlates to HVPG< vs HVPG=/>12 mmHg as follows: IL-1β (5.9+/−1.2 vs 22.9+/−1.2 pg/ml), IL-1Rα (53.1+/−12.0 vs 158.2+/−101.3 pg/ml), Fas-R (8.7+/−0.2 vs 9.3+/−0.5 ng/ml), VCAM-1 (1.1+/−0.09 vs 1.4+/−0.01; ng/ml), TNF-β (0.4+/−0.04 vs 0.6+/−0.06 ng/ml) and HSP-70 (42.6+/−1.2 vs 81.9+/−15.3 ng/ml).

The invention provides a method of correlating an inflammatory biomarker panel to hepatic vein pressure gradient (HVPG), comprising: correlating expression levels of two or more biomarkers from a biological sample of a patient with an HVPG measurement, wherein the biomarkers are selected from IL-1β, IL-1Rα, Fas-R, VCAM-1, TNF-β, HSP-70, IL-18, TLR9, lymphotoxin-β, glutamine, glutamine synthase, HSP-27, HSP-60, HSP-110, grp170, hyaluronan, homeocysteine, and angiotensin-II. The method further comprises performing esophagogastricduodenoscopy (EGD) on the patient when the expression levels correlate to an HVPG of greater than or equal to 12 mmHg.

The invention provides a method, wherein said biological sample is a biological fluid selected from the group consisting of whole blood, plasma, serum, or specific serum bacterial DNA. The invention provides a method, wherein said biomarker panel detects six biomarkers selected from the group consisting of IL-1β, IL-1Rα, Fas-R, VCAM-1, TNF-β and HSP-70.

The invention provides a method, wherein said assay is further correlated with demographic and clinical laboratory parameters selected from the group consisting of age, model for end-stage liver diseases (MELD), Child-Pugh Score (CPS), platelets, alanine aminotransferase (ALT), aspartate aminotransferase (AST), and at-risk alcohol use for indicating EGD to the patient or not indicating EGD for the patient.

The invention provides a non-invasive test to predict the presence severe portal hypertension at levels associated with the presence variceal bleeding and ascites. The invention provides a method, wherein a patient with non-clinically significant HVPG and esophageal varices is excluded from undergoing standard of care EGD.

The invention provides a kit for predicting HVPG and esophageal varices as a prognostic indicator for long term survival of a cirrhosis patient, comprising: a detection system comprising one or more reagents specific for detecting expression levels of a biomarker panel comprising two or more biomarkers selected from IL-1β (5.9+/−1.2 vs 22.9+/−1.2 pg/ml), IL-1Rα (53.1+/−12.0 vs 158.2+/−101.3 pg/ml), Fas-R (8.7+/−0.2 vs 9.3+/−0.5 ng/ml), VCAM-1 (1.1+/−0.09 vs 1.4+/−0.01; ng/ml), TNF-β (0.4+/−0.04 vs 0.6+/−0.06 ng/ml) and HSP-70 (42.6+/−1.2 vs 81.9+/−15.3 ng/ml) in a biological sample of said cirrhosis patient. The kit further includes instructions for using the kit for predicting the patient with non-clinically significant HVPG or esophageal varices, when the expression of said biomarker panel correlates with HVPG less than 12 mmHg threshold.

This invention provides a novel biomarker panel and non-invasive diagnostic test to measure hepatic vein pressure gradient (HVPG) and predict portal pressure and esophageal varices in cirrhotic patients by detecting and correlating a presence or expressions of the biomarker panel comprising one or more biomarkers with HVPG measurements, as well as clinically significant esophageal varices. In certain embodiments, the inventive biomarker panel comprises two or more specific inflammatory biomarkers including, but not limited to, IL-1β, IL-1Rα, Fas-R, VCAM-1, TNF-β, and HSP-70, as well as their related biomarkers, including but not limited to IL-18, toll-like receptor, such as TLR9, lymphotoxin-β, glutamine and glutamine synthase, and other heat shock proteins, such as, HSP-27, HSP-60, HSP-110, and grp170, and hyaluronan, homeocysteine, and angiotensin-II. In certain embodiments, the invention provides that a presence or expressions of at least two, at least three, at least four, at least five, and/or at least six of these biomarkers show significant correlations with HVPG measurements, predicting clinically significant portal pressure and/or esophageal varices.

In certain embodiments, the invention provides that the presence or expression of a biomarker panel comprising at least six (6) specific biomarkers: IL-1β, IL-1Rα, Fas-R, VCAM-1, TNF-β, and HSP-70, predicts non-clinically significant portal hypertension when the presence or expressions of these biomarkers correlate with HVPG less than 12 mmHg, which further suggests non-clinically significant esophageal varices (<5 mm). The invention provides that detection of the significant correlations between these biomarkers and HVPG less than 12 mmHg provides at least 86% accuracy excluding HVPG equal to or greater than 12 mmHg. The invention further suggests that patients with the presence or expressions of these biomarkers correlating with HVPG less than 12 mmHg can avoid undergoing the standard of care EGD in view of the non-clinically significant HVPG and esophageal varices.

On the other hand, the presence or expressions of these biomarkers correlating with HVPG equal to or greater than 12 mmHg suggests clinically significant portal hypertension, as well as clinically significant esophageal varices (>5 mm), which is the critical threshold for cirrhotic patients with variceal bleeding associated with portal hypertension in cirrhosis. Patients with the presence or expressions of these biomarkers correlating with HVPG equal to or greater than 12 mmHg should undergo the standard of care EGD in view of the clinically significant HVPG and likely esophageal varices. Methods for determining and correlating the presence or expression levels of one or more biomarkers (including mRNA, DNA, and/or other nucleic acid, and/or protein level of such biomarkers) are routine technologies and well known in the art by those skilled in the art.

The invention further provides that the non-invasive biomarker test correlates to or is in conjunction with established demographic and clinical laboratory parameters associated with liver diseases and/or cirrhosis, including but not limited to, age, model for end-stage liver diseases (MELD), Child-Pugh Score (CPS), platelets, alanine aminotransferase (ALT), aspartate aminotransferase (AST), and at-risk alcohol use.

Methods, kits, and/or devices for predicting portal pressure HVPG and esophageal varices as a prognostic indicator for long term survival of a cirrhosis patient by detecting the presence and/or the expression level of a specific biomarker panel comprising at least two, at least three, at least four, at least five, and at least six or more, biomarkers, including but not limited to, IL-1β, IL-1Rα, Fas-R, VCAM-1, TNF-β, and HSP-70, as well as their related biomarkers, including but not limited to IL-18, toll-like receptor, such as TLR9, lymphotoxin-β, glutamine and glutamine synthase, and other heat shock proteins, such as, HSP-27, HSP-60, HSP-110, and grp170, and hyaluronan, homeocysteine, and angiotensin-II, of the invention, are also provided.

Unless defined otherwise, all technical and scientific terms used herein have the same meaning as commonly understood by one of ordinary skill in the art to which the invention pertains. Other specifically defined terms are to be construed in a manner consistent with the definition provided herein. Although any methods and materials similar or equivalent to those described herein can be used in the practice for testing of the present invention, the preferred materials and methods are described herein. In describing and claiming the present invention, the following terminology will be used.

As used in this specification and the appended claims, the singular forms "a", "an" and "the" include plural referents unless the content clearly dictates otherwise. Thus, for example, reference to "an antibody" includes a combination of two or more antibodies, and the like.

Other embodiments and uses are apparent to one skilled in the art in light of the present disclosures. Those skilled in the art will appreciate that numerous changes and modifications can be made to the embodiments of the invention and that such changes and modifications can be made without departing from the spirit of the invention. It is, therefore, intended that the appended claims cover all such equivalent variations as fall within the true spirit and scope of the invention.

Throughout the specification various citations are referenced, and the entire content of each is hereby incorporated by reference. The following example is provided to describe the invention in more detail. It is intended to illustrate, not to limit the invention.

Example 1

Novel Inflammatory Biomarkers of Portal Pressure in Compensated Cirrhotic Patients The rationale for screening inflammatory serum biomarkers of the hepatic vein pressure gradient (HVPG) is based on the fact that portal hypertension is pathogenically related to liver injury and fibrosis, and that in turn these are associated with the activation of inflammatory pathways. This was a nested cohort study in the setting of a randomized, clinical trial to assess the development of gastroesophageal varices (GEV) (*N Engl J Med.* 353:2254; 2005). Patients had cirrhosis and portal hypertension but did not have GEV. A total of 90 patients that had baseline day-1 sera available were enrolled into the present study. The objective of this study was to determine whether inflammatory biomarkers in conjunction with clinical parameters could be used to develop a predictive paradigm for HVPG. The correlations between HVPG and IL-1β (P=0.0052); IL-1R-alpha (P=0.0085); Fas-R (P=0.0354) and serum VCAM-1 (P=0.0007) were highly significant. By using multivariate logistic regression analysis and selected parameters (TGFβ; HSP-70; at-risk alcohol use; and Child-Pugh B score) we could exclude HVPG equal or >12 mmHg with 86% accuracy (95% Confidence Interval; 67.78 to 96.16%) and the sensitivity was 87.01% (95% Confidence Interval; 69.68 to 96.34%). Therefore, the composite test could identify 86% of compensated cirrhotic patients with HVPG below 12 mmHg and prevent unnecessary esophagogastroduodenoscopy with its associated morbidity and costs in these patients. This diagnostic test was not efficient in predicting HVPG equal or >12 mmHg. A blood test for HVPG could also be performed in cirrhotic patients to prevent unnecessary esophagogastroduodenoscopy.

Methods

The study was a nested cohort study in the setting of an investigator-initiated, prospective, randomized, double-blind, placebo-controlled, clinical trial designed to evaluate the efficacy of nonselective beta-blockers in preventing GEV and the usefulness of measuring HVPG sequentially. The complete description of the trial has been published elsewhere (16). The protocol for conducting the current analysis of de-identified sera samples was approved by the UCSD Human Protection Program (Protocol #101569 on Aug. 16, 2012), the Research and Development Committee, VASDHS (Project #1159016 on Nov. 6, 2012) and the Yale Human Research Protection Program.

The patients were enrolled between August 1993 and March 1999. Eligible patients had cirrhosis and portal hypertension as defined by an HVPG of 6 mm Hg or greater, did not have GEV, and were older than 18 and less than 75 years of age. Exclusion criteria included ascites requiring diuretics, hepatocellular carcinoma, splenic or portal vein thrombosis, concurrent illness expected to decrease life expectancy to less than 1 year, the use of any drug or procedure affecting the splanchnic hemodynamic or portal pressure, primary biliary cirrhosis or primary sclerosing cholangitis, or any contraindications to beta blocker therapy, pregnancy, and alcohol intake during the dose titration phase. A total of 90 of the 213 subjects (39 from the Connecticut Center, 26 from the London Center, and 25 from the Boston Center) that had baseline day-1 sera available prior to drug or placebo treatment were enrolled into the present study. Full details of the clinical trial have been previously published (16).

The objective of this study was to determine whether novel biomarkers of inflammation measured in conjunction with established demographic and clinical laboratory parameters could be used to develop a predictive paradigm for HVPG.

The primary outcome was the analysis of clinical parameters (age and model for end-stage liver diseases [MELD]; Child-Pugh score [CPS] platelets; alanine aminotransferase (ALT); aspartate aminotransferase (AST)); and novel inflammatory serum biomarkers with respect to any correlations with HVPG. De-identified blood samples were then analyzed for novel inflammatory biomarkers. A multiplex peptide detection system (Human Sepsis Magnetic Bead Panels 1, 2 and 3; Milipore and Quansys Q-Plex Human Cytokine-Screen IR16-Plex; Quansys Biosciences) were utilized according to the manufacturer's protocol to determine inflammatory markers (interleukin [IL]-1α; IL-1β; IL-2; IL-4; IL-5; IL-6; IL-8; IL-10; IL-12; IL-13; IL-15; IL-17; interferon (IFN)-γ; tumor necrosis factor [TNF]-α; TNF-β; CCL22/MDC; CCL-17/TARC; IL-Rα; and IL-1RA; elastase-2; lactoferrin; thrombospondin-1; MIF; ICAM-1; Fas-L; Fas-R; VCAM-1; tPAI-1; granzyme-B; HSP-70; MIP-1α; MIP-1β; and MMP-8). Values were calculated from individual pixels using the MAGPIX analysis xPonent software and Q-View Imager system, respectively. An enzyme-linked immunoassay kit was used to determine serum LPS-binding protein (LPB) and CD-163 according to the manufacturer's protocol (BioVision and Aviscera Bioscience, respectively).

Individuals performing the laboratory tests were kept blinded to the subjects' demographics, clinical and portal pressure data.

The exploratory correlations were assessed with Pearson's correlation coefficient with 95% confidence intervals. Multiple linear regression analysis was performed to test for predictive values of demographic, clinical laboratory and novel inflammatory biomarkers to HVPG. The significance level was fixed at α=5% for all tests. All analyses were performed using the Analyse-it program.

Results

As outlined in Table 1, most subjects were middle age (mean 50.5+/−7 years; range 32 to 72 years), predominantly males (71%) and Caucasians (87%) with compensated cirrhosis (no ascites, no encephalopathy, no varices). Accordingly MELD score was low (9.5+/−2.3; range 6.4 to 16.3) as was the CPS (5.5+/−0.8; range 5.0 to 8.0) score. More than half of the subjects had chronic hepatitis C viral infection (55.6%) and 34% was at-risk alcohol use. At the time of HVPG measurement 6 patients had had a drink within the prior week but in the remaining 25 patients, last drink had been >1 month prior to HVPG measurements (with 12 having had the last drink >6 months prior to HVPG).

The etiology of cirrhosis was in its majority attributed to chronic hepatitis C (53%) and alcohol (28%). Subjects had mild to severe degrees of liver injury, judging by the levels of ALT (95.1+/−108.4; range 10 to 615 IU/ml) and AST (84.8+/−77.1; range 16 to 510 IU/ml), which most likely reflects a mild to severe level of liver inflammation. As expected for a cirrhotic cohort the platelets were relatively low (median 138.0; range 15 to $559 \times 10^3/\mu L$). No hepatitis C viral load was measured at the time of enrollment.

As anticipated, in this cirrhotic population selected for the absence of GEV, the HVPG was 10.9+/−3.9 mmHg (median: 10.3; range: 6.0 to 21.5 mmHg) (Table 1). The wedge hepatic vein pressure [WHVP] (19.3+/−5.2; median: 18.7; range: 7.0 to 30.0 mmHg) (3) was on average 8.4 mmHg higher than the HVPG (Table 1). Thirty of the 90 subjects (33.3%) had HVPG equal to or >12 mmHg, a critical threshold for variceal bleeding of cirrhosis associated with portal hypertension (3) and 60 subjects (66.6%) had HVPG<12 mmHg.

As depicted in Table 2, we found that HVPG correlated positively with age (P=0.0019); (MELD) (P<0.0001); CPS (P=0.0445); and platelets (P=0.0154) but the linear regression correlation $R^2$ was only 0.26 for age+MELD and lower for the other clinical indicators. There was no significant correlation between HVPG and either ALT or AST.

The correlations between HVPG and IL-1β (P=0.0052); IL-1Rα (P=0.0085); Fas-R (P=0.0354) and serum VCAM-1 (P=0.0007) were highly significant. There were no significant correlations between HVPG and other inflammatory biomarkers (LBP, CD-163, IL-1α, IL-4, IL-5, IL-6, IL-8, IL-10, IL-12, Il-13, IL-15, IL-17, CCL-17, CCL-22, TNFα, TNFβ, elastase-2, lactoferrin, thrombospondin-1, N-Gal, resistin, MIF, ICAM, Fas-L, tPAI-1, Granzyme-B, MIP-1α, MIP-1β, and MMP-8) as assessed with Pearson's correlation coefficient (Table 3).

Distribution analysis was performed for all of the variables by measuring skewness and kurtosis. Variables that did not have a normal distribution, judging by a skewness >0.5 were log transformed. All variables were analyzed by a two-sided t-test or chi-square test. Univariate logistic regression was run for HVPG<12 mmHg or HVPG equal or >12 mmHg (a clinically significant level of portal hypertension for variceal bleeding [36]). The four variables that were most significant (TNFβ [P=0.019]; HSP-70 [P=0.030]; at-risk alcohol use [P=0.003]; and Child-Pugh B score [P=0.034]) were submitted to multivariate logistic regression with backward elimination of the variables that did not add to the model. The four variables remained. These four variables were combined by logistic regression to a synthetic composite. ROC curves were produced for the four variables and the composite (area 0.767+/−0.057; asymptotic sigma P<0.0001; 95% CI 0.656 to 0.879) (FIG. 1). A scatter plot was drawn and a cut-point (CAT12) selected where probability of HVPG equal or >12 based on a natural break in the scatter plot. CAT12 groups were compared to actual HVPG<12. The composite test was statistically significant using several Chi-Square tests (Pearson Chi-Square P=0.017; Fisher's Exact Test P=0.025; Likelihood Ratio P=0.013; Linear-by-Linear Association P=0.018). The sensitivity, specificity, Positive Predictive Value (PPV) and Negative Predictive Value (NPV) were computed for actual HVPG cut at 12 mmHg. The NPV was 86.21% (significant 95% Confidence Interval; between 67.78 and 96.16%). Thus, if the equation predicts HVPG is <12 mmHg, then it will actually be <12 mmHg for 86% of the patients. The sensitivity was 87.01% (significant 95% Confidence Interval; between 69.68 and 96.34%). However, both the PPV (45.76%; significant 95% Confidence Interval; between 32.89 and 59.14%) and the specificity (43.86%; significant 95% Confidence Interval; between 30.93 and 57.56%) were relatively low.

TABLE 1

Baseline demographic and clinical characteristics of subjects (N = 90).

| Parameters | Numbers (%) |
| --- | --- |
| Sex (male) | 64 (71%) |
| Ethnicity | |
| Caucasians | 78 (87%) |
| Black | 4 (4%) |
| Hispanic | 4 (4%) |
| Others | 3 (3%) |
| Etiology | |
| Hepatitis C | 47 (52%) |
| Alcohol | 25 (28%) |
| Cryptogenic | 6 (7%) |
| Autoimmune | 5 (6%) |
| Hepatitis B | 4 (4%) |
| Others | 3 (3%) |

| Parameters | Mean (SD) | 95% CI | Percentile ($0^{th}$; $25^{th}$; $50^{th}$; $75^{th}$; $100^{th}$) |
| --- | --- | --- | --- |
| Age (years) | 50.5 (9.7) | 48.4 to 52.5 | 32; 44; 48; 57; 72 |
| MELD | 9.5 (2.3) | 9.0 to 10.0 | 6.4; 7.5; 8.9; 10.9; 16.3 |
| Child-Pugh (score) | 5.5 (0.8) | 5.3 to 5.6 | 5.0; 5.0; 5.0; 6.0; 8.0 |
| ALT (IU/ml) | 95.1 (108.4) | 72.4 to 117.8 | 10.0; 33.8; 59.5; 97.1; 615.0 |
| AST (IU/ml) | 84.8 (77.1) | 68.6 to 100.9 | 16.0; 40.8; 59.0; 97.3; 510.0 |
| Platelets ($\times 10^{-3}/\mu L$) | 144.8 (73.9) | 129.4 to 160.3 | 15.0; 98.3; 138.0; 173.6; 559.0 |
| HPVG | 10.9 (3.9) | 10.0 to 11.7 | 6.0; 8.0; 10.3; 12.7; 21.5 |
| WHVP | 19.3 (5.2) | 18.2 to 20.4 | 7.0; 15;0; 18.7; 23.0; 30.0 |

TABLE 2

Correlation of HVPG with demographic and clinical characteristics of subjects.

| Parameters | Pearson's P value |
|---|---|
| Age (years) | 0.0019* |
| MELD | 0.0001* |
| Age + MELD | 0.0001* |
| Child-Pugh (score) | 0.0445* |
| ALT (IU/ml) | 0.6123 |
| AST (IU/ml) | 0.5134 |
| Platelets ($\times 10^{-3}/\mu L$) | 0.0154* |

TABLE 3

Correlation between HVPG and inflammatory biomarkers.

| Inflammatory Biomarkers | Pearson's P value |
|---|---|
| VCAM-1 | 0.0007* |
| IL-1β | 0.0052* |
| IL-1Rα | 0.0085* |
| Fas-R | 0.0354* |
| ICAM-1 | 0.0609 |
| CD-163 | 0.0739 |
| Thrombospondin-1 | 0.0950 |
| Elastase-2 | 0.4105 |
| Lactoferrin | 0.7008 |
| LBP | 0.6297 |
| IL-1α | 0.0772 |
| IL-2 | 0.7130 |
| IL-4 | 0.4357 |
| IL-5 | 0.3703 |
| IL-6 | 0.2943 |
| IL-8 | 0.3585 |
| IL-10 | 0.5814 |
| IL-12 | 0.3990 |
| IL-13 | 0.7905 |
| IL-17 | 0.3132 |
| IFN-γ | 0.5065 |
| IL-1RA | 0.8545 |
| CCL-22 | 0.0955 |
| CCL-17 | 0.0905 |
| TNF-α | 0.0955 |
| TNF-β | 0.0905 |
| Fas-L | 0.0894 |
| Granzyme-B | 0.6713 |
| HSP-70 | 0.0894 |
| MIP-1α | 0.7681 |
| MIP-1β | 0.1162 |
| MMP-8 | 0.1183 |
| N-Gal | 0.5171 |
| Resistin | 0.3517 |
| MIF | 0.1662 |
| Resistin | 0.3517 |
| MIF | 0.1662 |

TABLE 4

Logistic regression analysis of HVPG biomarkers.

| | HVPG <12 mmHg | | HVPG ≥12 mmHg | | |
|---|---|---|---|---|---|
| Measure | Mean/N | SD/% | Mean/N | SD/% | P values |
| HSP70 | 4.23 | 1.12 | 3.64 | 1.32 | 0.030* |
| TNF-β | 412.08 | 336.82 | 594.58 | 350.18 | 0.019* |
| At risk of alcohol use | 19 | 33% | 21 | 66% | 0.003* |
| CPS-B score | 5 | 9% | 8 | 25% | 0.034* |

TABLE 5

Predictive value of the composite test for HVPG <12 mmHg

| Test Variable | Percent | 5% Confidence Intervals Test Variable | |
|---|---|---|---|
| Sensitivity | 87.09 | 69.67 | 96.33 |
| Specificity | 43.86 | 30.93 | 57.56 |
| Negative Predictive Value | 86.21 | 67.78 | 96.16 |
| Positive Predictive Value | 45.76 | 32.89 | 59.14 |

Furthermore, this study also indicates that the following biomarkers that correlate with HVPG: 1) IL-18 in view of the finding that LL-1β correlates with HVPG since active caspase-1 is essential for the concurrent cleavage of pro-IL-1β and pro-IL-18 into their mature, biologically active forms LL-1β and IL-18 (20; 21); 2) TLR-9 and Granulin in view of the finding that IL-1RA correlates with HVPG since TLG-9 signaling has been implicated in rapidly progressing tissue fibrosis and results in the activation of IL-1R pathways, and IL-1RA binds to the IL-1R inhibiting its signaling (20; 21; 25; 26); 3) lymphotoxin-β in view of the finding that TNFβ correlates with HVPG since TNFβ is secreted as a soluble polypeptide that forms heterotrimers with lymphotoxin-β (27); 4) the Heat Shock Proteins, such as HSP27, HSP-60, HSP-110, grp170 and their inducer glutamine in view of the finding that HSP-70 correlates with HVPG since glutamine, which is induced in hepatic acinar zone 3 by hypoxia (characteristic of cirrhosis with portal hypertension), stimulates transcription of Heat shock factor (HSF-1), a master regulator of Heat shock protein (HSP) (38; 39); and 5) VCAM-1 inducer: hyaluronan, homeocysteine and angiotensin-II, in view of the finding that that VCAM-1 correlates with HVPG since hyaluronan, homeocysteine and angiotensin-II induce expression of VCAM-1 (30; 31; 32).

In this example the novel inflammatory biomarkers IL-1β, IL-1Rα, Fas-R, VCAM-1, TNF-β and HSP-70 were found to be significantly correlated with HVPG in a compensated cirrhotic cohort. Also found were some demographic and clinical parameters correlated significantly with HVPG, including age; MELD; CPS; platelets; and at-risk alcohol use.

The rationale for screening inflammatory serum biomarkers of HVPG is based on the fact that portal hypertension is pathogenically related to liver injury and fibrosis (10; 11; 12; 13; 14; 15), and that in turn these are associated with the activation of inflammatory pathways (11; 12; 14; 15). Indeed, portal hypertension occurs in the presence of liver injury and inflammation even in the absence of liver fibrosis in fulminant acute liver failure and acute viral hepatitis (17; 18), indicating that liver injury and inflammation can be sufficient and critical for the development of portal hypertension (with 50% of the patients having portal pressures >12 mmHg. In addition, patients with chronic alcoholic liver disease in the absence of cirrhosis, may have HVPG>12 mmHg and develop esophageal varices, suggesting that in addition to and sometimes in the absence of liver fibrosis, hepatocyte injury and inflammation affect the portal pressure (19).

Inflammatory pathways can be activated by bacterial translocation (or translocation of LPS and DNA) from the intestine to the portal vein circulation that occurs in patients with cirrhosis and portal hypertension (10; 13; 14). Bacterial/LPS/DNA translocation leads to activation of toll-like receptors (TLRs) and their induction of signaling pathways resulting in the secretion of inflammatory mediators into the circulation (12; 13). In support of these findings, the activation of these signaling inflammatory pathways may be clinically inconspicuous but could be detected by measuring hemodynamic effects or humoral mediators in blood (10; 12; 13). The increase in HVPG after a meal significantly correlated with serum bacterial DNA concentration, suggesting a causal effect between HVPG and bacterial translocation (10).

A critical inflammatory signaling pathway is the Inflammasome. It was found that IL-1β, a critical cytokine product of the Inflammasome, and its receptor IL-1Rα correlated significantly with HVPG (20; 21). Active caspase-1 is essential for the cleavage of pro-IL-1β into its mature, biologically active form IL-1β (20). Based on this rationale anti-caspase drugs are being analyzed in Clinical Phase-2 Studies to ameliorate hepatocyte injury (22). Similarly, polymorphisms of the TLR-9, which initiates signals activating the Inflammasome (23; 24; 25), have been implicated in rapidly progressing tissue fibrosis (26).

It was also found that TNF-β, a product of activated T and B lymphocytes and a member of the TNF-α superfamily, correlates significantly with HVPG. TNFβ is secreted as a soluble inflammatory polypeptide that forms heterotrimers with lymphotoxin-β and mediates a large variety of inflammatory, immunostimulatory, and antiviral responses (27), which are relevant to the cohort of cirrhotic patients etiologically linked to chronic HCV infection and alcohol use. In addition, the serum Fas-R, another member of the TNF-α cell death receptor superfamily, which may be increased with liver injury and inflammation (28; 29), also correlated with HVPG.

A highly significant correlation between HVPG and serum VCAM-1, a product of endothelial cells was found (30; 31; 32). The increase in circulating endothelial cells in cirrhotic patients is congruent with these findings (33). In addition, bacterial DNA translocation is associated with intrahepatic endothelial dysfunction in patients with cirrhosis (10). Hyaluronan, homeocysteine and angiotensin-II can induce the expression of VCAM-1 synthesis (30; 31; 32). All of these factors are mechanistically related to cirrhosis. Serum hyaluronan and homeocysteine are increased in liver fibrosis while angiotensin-II stimulates liver fibrosis (34; 35; 36; 37). Therefore, the relationship between hyaluronan, homeocysteine and angiotensin II with HVPG can be established.

The heat shock protein (HSP)-70 correlated significantly with HVPG in the logistic regression analysis. Of interest, glutamine, an amino acid induced in hepatic acinar zone 3 by hypoxia (characteristic of cirrhosis with portal hypertension), stimulates transcription of heat shock factor (HSF)-1, an inducer of HSP-70 (38; 39). Thus, glutamine and glutamine synthethase can also be biomarkers of HVPG.

Presently, a significant correlation was found using Pearson's test of HVPG with novel inflammatory biomarkers (IL-1β, IL-1Rα, Fas-R, and VCAM-1). By using multivariate logistic regression analysis and selected parameters (TNFβ; HSP-70; at-risk alcohol use; and Child-Pugh B score) HVPG equal or >12 mmHg was excluded with 86% accuracy (significant 95% Confidence Interval; between 67.78 and 96.16%) and the sensitivity was 87.01% (significant 95% Confidence Interval; between 69.68 and 96.34%). Therefore, the composite test could identify 86% of compensated cirrhotic patients with HVPG below 12 mmHg and prevent unnecessary EGDs with their associated morbidity and costs in these patients. As it is the case for estimating HVPG by measuring liver stiffness (LS) with transient elastography (9), this diagnostic test was not efficient in predicting HVPG equal or >12 mmHg (PPV: 45.76%; Specificity: 43.86%). Therefore, the ROC was only moderately accurate (area 0.767+/−0.057; asymptotic sigma P<0.0001; 95% CI 0.656 to 0.879) and similar to the ROC curve (0.76+/−0.07; 95% confidence index 0.60-0.87) reported for the prediction of HVPG by LS-elastography for all cirrhotic patients in their cohort (40).

Although LS has been proposed for predicting HVPG, the method as currently used has several technical and logistic limitations making the measurement not interpretable in a large percentage of patients with cirrhosis (41). The exclusion criteria for LS include obesity, ascites, congestive heart failure, extrahepatic cholestasis and severe liver inflammation related to HCV infection (9; 42). Also, in cirrhotic patients LS values increased by 25% after a light meal, as compared with fasting patients, suggesting a spurious postprandial increase in the predicted HVPG in cirrhosis (43).

Vizzutti and coworkers (40) reported a good correlation between LS and HVPG in the entire cohort ($R^2$=0.61; P<0.0001) in 61 consecutive selected patients with HCV-related chronic liver disease. Although the correlation between LS and HVPG was very good for HVPG values less than 10 or 12 mm Hg ($R^2$=0.72, P=0.0001 and $R^2$=0.67 P<0.0001, respectively) it was poor for HVPG>10 mmHg and >12 mmHg ($R^2$=0.35, P=0.0001 and $R^2$=0.17 P<0.02, respectively) (9). Berzigotti and coworkers (44) have shown that LS provides excellent results when combined with platelets count and spleen size (LSPS). Analyses of LSPS were effective in identifying patients with clinically significant HVPG; they correctly classified 83% of patients in the training set (N: 117) and 85% in the validation set (N: 56). Berzigotti and coworkers (45) also reported that obesity was present in 30% of a cohort of compensated cirrhotic patients. Thus, in evaluating HVPG by LS including all subjects (an 'intention to diagnose' study), the 85% predictive accuracy of LSPS reported by Berzigotti and coworkers (44) would be applicable to only about 70% of those subjects, resulting in a correct classification of HVPG in about 60% of the patients (85%×0.70).

Colecchia and coworkers suggested using spleen stiffness (SS) measurement as a screening test for the indication of esophagogastroduodenoscopy (EGD). Using an intention-to-diagnose approach only 7 of 113 (7.1%) screened patients would have wrongly avoided esophagogastroduodenoscopy (46). Similarly, Sharma and coworkers found that SS≥40.8 kPa had high sensitivity (94%), specificity (76%), positive predictive value (91%), negative predictive value (84%), and diagnostic accuracy (86%) for predicting EV (47). However, in the latter study, out of 270 patients SS was performed only in 174 patients since 70 patients were excluded before performing the SS measurement (due to ascites, alcohol abuse and hepatitis reactivation) and in 26 the SS measurement could not be obtained. Thus, the intention-to treat would markedly reduce both the sensitivity of the technique (47).

References

1. Bosch J, Abraldes J G, Berzigotti A, Garcia-Pagan J C. (2008). Portal hypertension and gastrointestinal bleeding. Semin Liver Dis. 28(1):3-25. PMID 18293274.
2. Report 04-5491. Executive Summary. Action Plan for Liver Disease Research. U.S. Department of Health and Human Services: (2004) NIH. pp. 1-6.
3. Groszmann R J, Bosch J, Grace N, Conn H O, Garcia-Tsao G, Navasa M, et al. Hemodynamic events in a prospective randomized trial of propranolol vs placebo in the prevention of the first variceal hemorrhage. Gastroenterology 1990; 99:1401-1407

4. Burroughs A K, Groszmann R, Bosch J, Grace N, Garcia-Tsao G, Patch D, Garcia-Pagan J C, Dagher L. (2002). Assessment of therapeutic benefit of antiviral therapy in chronic hepatitis C: is hepatic venous pressure gradient a better end point? Gut. 50(3):425-7. PMID: 11839726

5. Grace N D. (2011). Patients with clinically significant portal hypertension caused by hepatitis C virus cirrhosis respond poorly to antiviral therapy. Clin Gastroenterol Hepatol. 9(7):536-8. PMID: 21554988

6. Armonis A, Patch D, Burroughs A. (1997). Hepatic venous pressure measurement: an old test as a new prognostic marker in cirrhosis? Hepatology. 25(1):245-8. PMID: 8985299

7. García-Pagán J C, Morillas R, Bañares R, Albillos A, Villanueva C, Vila C, Genescà J, Jimenez M, Rodriguez M, Calleja J L, Balanzó J, García-Durán F, Planas R, Bosch J; Spanish Variceal Bleeding Study Group. (2003). Propranolol plus placebo versus propranolol plus isosorbide-5-mononitrate in the prevention of a first variceal bleed: a double-blind RCT. Hepatology. 37(6):1260-6. PMID: 12774003

8. Schepke M, Raab P, Hoppe A, Schiedermaier P, Brensing K A, Sauerbruch T. (2000). Comparison of portal vein velocity and the hepatic venous pressure gradient in assessing the acute portal hemodynamic response to propranolol in patients with cirrhosis. Am J Gastroenterol. 95(10):2905-9. PMID: 11051366

9. Castera L, Pinzani M, Bosch J. (2012). Non invasive evaluation of portal hypertension using transient elastography. J Hepatol. 56(3):696-703. PMID: 21767510

10. Bellot P, García-Pagán J C, Francés R, Abraldes J G, Navasa M, Pérez-Mateo M, Such J, Bosch J. (2010). Bacterial DNA translocation is associated with systemic circulatory abnormalities and intrahepatic endothelial dysfunction in patients with cirrhosis. Hepatology. 52(6):2044-52. PMID: 20979050

11. Chung R and Podolsky D. (2005). Cirrhosis and its Complications. In: Harrison's Principles of Internal Medicine, New York: McGraw-Hill, pp. 1754-1767.

12. Francés R, Rodríguez E, Muñoz C, Zapater P, De la M L, Ndongo M, Pérez-Mateo M, Such J. (2005). Intracellular cytokine expression in peritoneal monocyte/macrophages obtained from patients with cirrhosis and presence of bacterial DNA. Eur J Gastroenterol Hepatol. 17(1):45-51. PMID: 15647640

13. Francés R, Zapater P, González-Navajas J M, Muñoz C, Caño R, Moreu R, Pascual S, Bellot P, Pérez-Mateo M, Such J. (2008). Bacterial DNA in patients with cirrhosis and noninfected ascites mimics the soluble immune response established in patients with spontaneous bacterial peritonitis. Hepatology. 47(3):978-85. PMID: 18306221

14. Chojkier M. (1998). Regulation of collagen gene expression. In: Strain A, Diehl A, editors. Liver growth and repair. London: Chapman & Hall. pp. 430-450.

15. Picchiotti R, Mingazzini P L, Scucchi L, Bressan M, Di Stefano D, Donnetti M, Feroci L. (1994). Correlations between sinusoidal pressure and liver morphology in cirrhosis. J Hepatol. 20(3):364-9. PMID: 8014448

16. Groszmann R J, Garcia-Tsao G, Bosch J, Grace N D, Burroughs A K, Planas R, Escorsell A, Garcia-Pagan J C, Patch D, Matloff D S, Gao H, Makuch R; Portal Hypertension Collaborative Group. (2005). Beta-blockers to prevent gastroesophageal varices in patients with cirrhosis. N Engl J Med. 353(21):2254-61. PMID: 16306522

17. Lebrec D., Nouel O, Bernuau J, Rueff B, and Benhamou J P. Portal hypertension in fulminant viral hepatitis. Gut, 21, 962-964, 1980.

18. Valla D, Flejou J F, Lebrec D, Bernuau J, Rueff B, Salzmann J L, Benhamou J P. (1989). Portal hypertension and ascites in acute hepatitis: clinical, hemodynamic and histological correlations. Hepatology. 10(4):482-7. PMID: 2777210

19. Reynolds T B, Hidemura R, Michel H and Peters R. Portal Hypertension Without Cirrhosis in Alcoholic Liver Disease Ann Intern Med. 1 Mar. 1969; 70 (3):497-506

20. Boraschi D, Tagliabue A. (2006). The interleukin-1 receptor family. Vitam Horm. 74:229-54. PMID: 17027517

21. Elkon K B. (2007). IL-1alpha responds to necrotic cell death. Nat Med. 13(7):778-80. PMID: 17618263

22. Ratziu V, Sheikh M Y, Sanyal A J, Lim J K, Conjeevaram H, Chalasani N, Abdelmalek M, Bakken A, Renou C, Palmer M, Levine R A, Bhandari B R, Cornpropst M, Liang W, King B, Mondou E, Rousseau F S, McHutchison J, Chojkier M. (2012). A phase 2, randomized, double-blind, placebo-controlled study of GS-9450 in subjects with nonalcoholic steatohepatitis. Hepatology. 55(2):419-28. PMID: 22006541

23. Chockalingam A, Cameron J L, Brooks J C, Leifer C A. (2011). Negative regulation of signaling by a soluble form of toll-like receptor 9. Eur J Immunol. 41(8):2176-84. PMID: 21604257

24. Franchi L, Eigenbrod T, Muñoz-Planillo R, Nuñez G. (2009). The inflammasome: a caspase-1-activation platform that regulates immune responses and disease pathogenesis. Nat Immunol. 10(3):241-7. PMID: 19221555

25. Park B, Buti L, Lee S, Matsuwaki T, Spooner E, Brinkmann M M, Nishihara M, Ploegh H L. (2011). Granulin is a soluble cofactor for toll-like receptor 9 signaling. Immunity. 34(4):505-13. PMID: 21497117

26. Trujillo G, Meneghin A, Flaherty K R, Sholl L M, Myers J L, Kazerooni E A, Gross B H, Oak S R, Coelho A L, Evanoff H, Day E, Toews G B, Joshi A D, Schaller M A, Waters B, Jarai G, Westwick J, Kunkel S L, Martinez F J, Hogaboam C M. (2010). TLR9 differentiates rapidly from slowly progressing forms of idiopathic pulmonary fibrosis. Sci Transl Med. 2(57):57ra82. PMID: 21068441

27. Haybaeck J, Zeller N, Wolf M J, Weber A, Wagner U, Kurrer M O, Bremer J, Iezzi G, Graf R, Clavien P A, Thimme R, Blum H, Nedospasov S A, Zatloukal K, Ramzan M, Ciesek S, Pietschmann T, Marche P N, Karin M, Kopf M, Browning J L, Aguzzi A, Heikenwalder M. (2009). A lymphotoxin-driven pathway to hepatocellular carcinoma. Cancer Cell. 16(4):295-308. PMID: 19800575

28. Izquierdo J M, Majós N, Bonnal S, Martínez C, Castelo R, Guigó R, Bilbao D, Valcárcel J. (2005). Regulation of Fas alternative splicing by antagonistic effects of TIA-1 and PTB on exon definition. Mol Cell. 19(4):475-84. PMID: 16109372

29. Wajant H. (2002). The Fas signaling pathway: more than a paradigm. Science. 296(5573):1635-6. PMID: 12040174

30. Carluccio M A, Ancora M A, Massaro M, Carluccio M, Scoditti E, Distante A, Storelli C, De Caterina R. (2007). Homocysteine induces VCAM-1 gene expression through NF-kappaB and NAD(P)H oxidase activation: protective role of Mediterranean diet polyphenolic antioxidants. Am J Physiol Heart Circ Physiol. 293(4):H2344-54. PMID: 17586618

31. Oertli B, Beck-Schimmer B, Fan X, Wüthrich R P. (1998). Mechanisms of hyaluronan-induced up-regulation of ICAM-1 and VCAM-1 expression by murine kidney tubular epithelial cells: hyaluronan triggers cell adhesion molecule expression through a mechanism involving activation of nuclear factor-kappa B and activating protein-1. J Immunol. 161(7):3431-7. PMID: 9759861
32. Pueyo M E, Gonzalez W, Nicoletti A, Savoie F, Arnal J F, Michel J B. (2000). Angiotensin II stimulates endothelial vascular cell adhesion molecule-1 via nuclear factor-kappaB activation induced by intracellular oxidative stress. Arterioscler Thromb Vasc Biol. 20(3):645-51. PMID: 10712386
33. Abdelmoneim S S, Talwalkar J, Sethi S, Kamath P, Fathalla M M, Kipp B R, Campion M B, Clayton A C, Halling K C, Shah V H. (2010). A prospective pilot study of circulating endothelial cells as a potential new biomarker in portal hypertension. Liver Int. 30(2):191-7. PMID: 19840257
34. Bataller R, Gäbele E, Parsons C J, Morris T, Yang L, Schoonhoven R, Brenner D A, Rippe R A. (2005). Systemic infusion of angiotensin II exacerbates liver fibrosis in bile duct-ligated rats. Hepatology. 2005 May; 41(5): 1046-55. PMID: 15841463
35. Bosy-Westphal A, Ruschmeyer M, Czech N, Oehler G, Hinrichsen H, Plauth M, Lotterer E, Fleig W, Müler M J. (2003). Determinants of hyperhomocysteinemia in patients with chronic liver disease and after orthotopic liver transplantation. Am J Clin Nutr. 77(5):1269-77. PMID: 12716682
36. Engström-Laurent A, Lööf L, Nyberg A, Schröder T. (1985). Increased serum levels of hyaluronate in liver disease. Hepatology. 5(4):638-42. PMID: 4018736
37. Torres L, García-Trevijano E R, Rodríguez J A, Carretero M V, Bustos M, Fernández E, Eguinoa E, Mato J M, Avila M A. (1999). Induction of TIMP-1 expression in rat hepatic stellate cells and hepatocytes: a new role for homocysteine in liver fibrosis. Biochim Biophys Acta. 1455(1):12-22. PMID: 10524225
38. Wang X Y, Kazim L, Repasky E A, Subjeck J R. (2001). Characterization of heat shock protein 110 and glucose-regulated protein 170 as cancer vaccines and the effect of fever-range hyperthermia on vaccine activity. J Immunol. 166(1):490-7. PMID: 11123328.
39. Xue H, Slavov D, Wischmeyer P E. (2012). Glutamine-mediated dual regulation of heat shock transcription factor-1 activation and expression. J Biol Chem. 287(48): 40400-13. PMID: 23055521
40. Vizzutti F, Arena U, Romanelli R G, Rega L, Foschi M, Colagrande S, Petrarca A, Moscarella S, Belli G, Zignego A L, Marra F, Laffi G, Pinzani M. (2007). Liver stiffness measurement predicts severe portal hypertension in patients with HCV-related cirrhosis. Hepatology. 45(5): 1290-7. PMID: 17464971
41. Castéra L, Foucher J, Bernard P H, Carvalho F, Allaix D, Merrouche W, Couzigou P, de Lédinghen V. (2010). Pitfalls of liver stiffness measurement: a 5-year prospective study of 13,369 examinations. Hepatology. 51(3): 828-35. PMID: 20063276
42. Sandrin L, Fourquet B, Hasquenoph J M, Yon S, Fournier C, Mal F, Christidis C, Ziol M, Poulet B, Kazemi F, Beaugrand M, Palau R. (2003). Transient elastography: a new noninvasive method for assessment of hepatic fibrosis. Ultrasound Med Biol. 29(12):1705-13. PMID: 14698338
43. Berzigotti A, De Gottardi A, Vukotic R, Siramolpiwat S, Abraldes J G, García-Pagán J C, Bosch J. (2013). Effect of meal ingestion on liver stiffness in patients with cirrhosis and portal hypertension. PLoS One. 8(3):e58742. PMID: 23520531
44. Berzigotti A, Seijo S, Arena U, Abraldes J G, Vizzutti F, García -Pagán J C, Pinzani M, Bosch J. (2013). Elastography, spleen size, and platelet count identify portal hypertension in patients with compensated cirrhosis. Gastroenterology. 144(1):102-111.e1. PMID: 23058320
45. Berzigotti A, Garcia-Tsao G, Bosch J, Grace N D, Burroughs A K, Morillas R, Escorsell A, Garcia-Pagan J C, Patch D, Matloff D S, Groszmann R J; Portal Hypertension Collaborative Group. (2011). Obesity is an independent risk factor for clinical decompensation in patients with cirrhosis. Hepatology. 54(2):555-61. PMID: 21567436.
46. Colecchia A, Montrone L, Scaioli E, Bacchi-Reggiani M L, Colli A, Casazza G, Schiumerini R, Turco L, Di Biase A R, Mazzella G, Marzi L, Arena U, Pinzani M, Festi D. Measurement of spleen stiffness to evaluate portal hypertension and the presence of esophageal varices in patients with HCV-related cirrhosis. Gastroenterology. 2012; 143: 646-54.
47. Sharma P, Kirnake V, Tyagi P, Bansal N, Singla V, Kumar A, Arora A. Spleen Stiffness in Patients With Cirrhosis in Predicting Esophageal Varices. Am J Gastroenterol 2013; 108:1101-1107.

Example 2

Biomarkers to Exclude the Presence of Clinically Significant Esophageal Varices

This example focuses on the validation of previously discovered biomarkers that are used to predict the absence of clinically significant esophageal varices (>5 mm as measured by esophagogastroduodenoscopy [EGD]) in cirrhotic patients, providing greater predictive insights on which cirrhotic patients lack clinically significant esophageal varices and, therefore, are excluded from standard of care (SOC) screening EGD. At present, all cirrhotic patients must undergo EGD screening for esophageal varices as standard of care (54). This subjects a subset of this cohort, without clinically significant esophageal varices to an unnecessary procedure with its potential complications (sedation-induced respiratory depression; pulmonary aspiration; paradoxical excitation in patients on narcotics and sedatives; pharyngeal injury and EGD-induced bleeding from varices), thus, also save significant human and financial medical resources (~$10,000 per unneeded EGD).

The annual worldwide mortality from liver cirrhosis is approximately 800,000 (2; 48). Excessive tissue repair in chronic liver diseases induced by alcoholic, viral, toxic, immunologic, and metabolic disorders (11), results in the deposition of scar tissue and the development of cirrhosis (14). Chronic liver disease and cirrhosis account for approximately 27,000 deaths in the United States each year.

The development of esophageal varices and esophageal variceal hemorrhage are the complications of cirrhosis that result most directly from portal hypertension (5; 16). Esophageal varices are the most relevant complication of portal hypertension because their rupture results in variceal hemorrhage, the most common lethal complication of cirrhosis (6-8; 22; 23). A threshold of portal pressure (Hepatic Vein Pressure Gradient (HVPG)) of 12 mmHg is needed to develop clinically significant esophageal varices (5 mm) (3; 4; 41). All cirrhotic patients with clinically significant esophageal varices (5 mm) have HVPG equal to or greater than 12 mmHg. No cirrhotic patient develops clinically significant esophageal varices with a HVPG of <12 mmHg.

Esophageal varices are present in approximately 50% of patients with cirrhosis (54). Their presence correlates with the severity of liver disease; while only 40% of Child A (compensated cirrhotic patients without ascites, encephalopathy or variceal bleeding) have esophageal varices, they are present in ~85% of Child C (decompensated cirrhotic patients with ascites, encephalopathy or variceal bleeding) (54).

Variceal hemorrhage occurs at a yearly rate of 5-15%, and the most important predictor of hemorrhage is the size of varices, as measured by EGD, with the highest risk of first hemorrhage (15% per year) occurring in patients with large varices (>5 mm) (4; 54). The gold standard of clinical care for the diagnosis of varices is EGD (54).

The frequency of surveillance endoscopies in patients with no or small varices depends on their natural history. As this is a very subjective and imprecise variable of diagnosis, the clinical challenge is to provide a more exacting way to triage the procedures needed for these patients. The AASLD Guidelines recommends that EGD should be performed once a diagnosis of cirrhosis is established (54). In patients with compensated cirrhosis who have no varices on a first screening endoscopy, the EGD should be repeated in 2-3 years (4; 54). In those who have small varices (1-5 mm) on primary screening, the EGD should be repeated in 1-2 years (6; 54). In the presence of decompensated cirrhosis, EGD should be repeated at yearly intervals (49; 50; 54). The minimally invasive blood test using novel biomarkers could be of greatest potential impact in its use to exclude the compensated cirrhotic patients with no or small varices. It could spare these patients unnecessary risk from an unneeded procedure and save the medical resources involved with these procedures. A lower percentage of the decompensated Child-B and C cirrhotic patients could also benefit from predictive biomarkers since they may not have clinically significant esophageal varices and if the other complications of cirrhosis (ascites and encephalopathy) do not affect the accuracy of the biomarkers.

There is not an FDA-approved non-invasive test for the diagnosis of esophageal varices. There is not competing technology that measures esophageal varices directly, except capsule endoscopy.

Liver Stiffness (LS) has been proposed for predicting HVPG (and consequently, esophageal varices) but the method as currently used has several technical and logistic limitations making the measurement not interpretable in a large percentage of patients with cirrhosis (41). The exclusion criteria for LS include obesity, ascites, congestive heart failure, extrahepatic cholestasis and severe liver inflammation related to HCV infection (9; 42). Also, in cirrhotic patients LS values increased by 25% after a light meal, as compared with fasting patients, suggesting a spurious postprandial increase in the predicted HVPG (and esophageal varices) in cirrhosis (43). Vizzutti and coworkers (40) reported a good correlation between LS and HVPG in the entire cohort ($R^2=0.61$; $P<0.0001$) in 61 selected patients with HCV-related chronic liver disease. Although the correlation between LS and HVPG was very good for HVPG values less than 10 or 12 mm Hg ($R^2=0.72$, $P=0.0001$ and $R^2=0.67$ $P<0.0001$, respectively) it was poor for HVPG>10 mmHg and >12 mmHg ($R^2=0.35$, $P=0.0001$ and $R^2=0.17$ $P<0.02$, respectively) (9).

Berzigotti and coworkers (44) have shown that LS provides excellent results when combined with platelets count and spleen size (LSPS). Analyses of LSPS were effective in identifying patients with clinically significant HVPG (and eventually, esophageal varices); they correctly classified 83% of patients in the training set (N: 117) and 85% in the validation set (N: 56). Berzigotti and coworkers (45) also reported that obesity was present in 30% of a cohort of compensated cirrhotic patients. Thus, in evaluating HVPG by LS including all subjects (an intention-to-diagnose' study), the 85% predictive accuracy of LSPS reported by Berzigotti and coworkers (44) would be applicable to only about 70% of those subjects, resulting in a correct classification of HVPG in about 60% of the patients (85%×0.70).

Colecchia and coworkers suggested using Spleen Stiffness (SS) measurement as a screening test for the indication of EGD. Using an intention-to-diagnose approach 35 of 141 (25%) screened patients would have wrongly avoided EGD or not been able to be tested (46). Similarly, when using an intention-to-diagnose approach, the results from Sharma and coworkers indicate only a 54% negative predictive value for the diagnosis of esophageal varices (84% NPV×0.35% of patients excluded from the procedure). Out of 270 patients SS was performed only in 174 patients (65%) since 96 patients were excluded (70 due to ascites, alcohol abuse and hepatitis reactivation and 26 where the measurement could not be obtained). Thus, applying an intention-to-diagnose would markedly reduce both the sensitivity and specificity of the technique, rendering it unsuitable for clinical care (47).

Esophageal capsule endoscopy is a procedure that may be valuable. Two recent pilot studies show that capsule endoscopy is a safe and well-tolerated way to diagnose esophageal varices (51; 52), although its sensitivity remains to be established. Thus, it remains to be determined whether capsule endoscopy will play a role in screening for esophageal varices if additional larger studies support its use (54). All of these potentially alternative techniques to diagnose esophageal varices, including capsule endoscopy, require expensive equipment and medical expertise that is not available to the average patient in clinical settings outside of highly developed medical centers.

There is a full agreement among experts that the development of a non-invasive test to exclude the presence of clinically significant esophageal varices (>5 mm) could have clinical relevance (6; 54). The NIH Action Plan for Liver Diseases (Chapter 13—Complications of Liver Diseases) indicates that the development of noninvasive means to screen for clinically significant esophageal varices is a priority (2). In this context, it was shown in the above Example 1, in a small but well characterized cirrhotic cohort (16), that some low levels of some selected inflammatory biomarkers are able to correctly exclude HVPG equal to or >12 mmHg with a high sensitivity (87%) and high negative predictive value (86%).

Thus, if the biomarkers can exclude patients with clinically significant portal pressure (HVPG equal to or >12 mmHg); and clinically significant portal pressure is indispensable to develop clinically significant esophageal varices (>5 mm); then, these biomarkers can also be able to exclude clinically significant esophageal varices. If the correlation obtained with the biomarkers to exclude 86% of the non-clinically significant HVPG correlates with the exclusion of clinically significant esophageal varices, the clinical innovation of the biomarkers could be outstanding and physiologically reasonable since clinically significant esophageal varices do not develop below a portal pressure threshold of 12 mmHg of HVPG, and this is the mechanistic threshold activity of discovery of the novel biomarkers (See Example 1).

The ability to predict which cirrhotic patients are not in need of a screening EGD with a blood test could revolutionize clinical management of patients with chronic liver diseases, as well as aid in the design and performance of clinical research into the complications of cirrhosis (1; 2; 4; 54). Given that 6 inflammatory biomarkers were recently found to serve as a non-invasive test to predict the absence of clinically significant portal hypertension (See Example 1 above), these biomarkers could also predict the absence of clinically significant esophageal varices (2), and therefore avoid the screening EGD in these particular patients. In Example 1, 6 biomarkers were identified that provide an 87% sensitivity to exclude clinically significant portal hypertension. The objective of this example is to analyze whether these 6 biomarkers provide the same efficacy to exclude clinically significant esophageal varices (>5 mm).

Results

Most subjects were middle age (mean 50.5+/−7 years; range 32 to 72 years), predominantly males (71%) and Caucasians (87%) with compensated cirrhosis. Accordingly, MELD score was low (9.5+/−2.3; range 6.4 to 16.3) as was the Child-Pugh score (5.5+/−0.8; range 5.0 to 8.0. According to Drs. Bosch, Garcia-Tsao and coworkers (9, 54), the novel non-invasive test will potentially have the greatest clinical impact in the subset of compensated cirrhotic patients with a ~50% probability of having esophageal varices. The alcohol use was defined in the original cohort by Drs. Groszmann, Garcia-Tsao and coworkers (16) as the consumption of >60 g alcohol/day (the duration of said alcohol use ranged from 2 to 45 years.

The etiology of cirrhosis was in its majority attributed to chronic hepatitis C (53%) and alcoholism (28%). Subjects had mild to severe degrees of liver injury, judging by the levels of ALT (95.1+/−108.4; range 10 to 615 IU/ml) and AST (84.8+/−77.1; range 16 to 510 IU/ml), which would be congruent with mild to severe level of liver inflammation. As expected for a cirrhotic cohort the platelets were relatively low (median 138.0; range 15 to 559×10$^3$/μL). Unfortunately, no hepatitis C viral load was measured at the time of enrollment.

In the published study, thirty of the 90 subjects (33%) had HVPG equal to or >12 mmHg, a critical threshold for clinically significant esophageal varices of cirrhosis (3; 41), and 60 subjects (66%) had HVPG<12 mmHg. The HVPG range was 6.0 to 21.5 mmHg in the cohort (normal HVPG is 1-5 mmHg).

The goal for a test using these novel biomarkers is the exclusion of EGD screening for those patients with a score below the cut-off value that is predictive of clinically significant esophageal varices. To reach these goals a study reported in above Example 1 was completed using archival blood samples obtained during the measurement of portal pressure in a well characterized cohort of cirrhotic patients from Yale, Harvard and London Royal Free Medical Centers (16).

As reported in above Example 1, six biomarkers: IL-1β, IL-1Rα, Fas-R, VCAM-1, TNF-β and HSP-70 are found to be significantly correlated with HVPG in a cirrhotic cohort (16). The Pearson's correlations between HVPG and serum IL-1β (P=0.0052); IL-1R-α (P=0.0085); Fas-R (P=0.0354); VCAM-1 (P=0.0007); TNF-β (P=0.030) and HSP-70 (P=0.019) were highly significant. The values of the biomarkers for HVPG< vs HVPG=/>12 mmHg were for IL-1β (5.9+/−1.2 vs 22.9+/−1.2 pg/ml), IL-1Rα(53.1+/−12.0 vs 158.2+/−101.3 pg/ml), Fas-R (8.7+/−0.2 vs 9.3+/−0.5 ng/ml), VCAM-1 (1.1+/−0.09 vs 1.4+/−0.01; ng/ml), TNF-β (0.4+/−0.04 vs 0.6+/−0.06 ng/ml) and HSP-70 (42.6+/−1.2 vs 81.9+/−15.3 ng/ml). By using novel biomarkers and known clinical parameters (TGFβ; HSP-70; alcoholism; and Child-Pugh B score) patients with HVPG equal or >12 mmHg were identified with 86% accuracy (95% Confidence Interval; 67.78 to 96.16%) and 87.01% sensitivity (95% Confidence Interval; 69.68 to 96.34%). Therefore, the composite test presented in Example 1 would identify 86% of cirrhotic patients with HVPG below 12 mmHg and could prevent unnecessary EGDs with its associated morbidity and costs in these patients.

The studies presented in Example 1 had a similar distribution of HCV, alcohol and autoimmune etiologies for cirrhosis in the cohort with HVPG<12 mmHg and with HVPG equal or greater than 12 mmHg. Thus, the biomarkers are not the results of confounding variables such as the consequence of unbalanced distribution of cases of liver diseases among these patients. The test is not intended to predict HVPG equal or >12 mmHg, as it is not designed to replace measurements of portal pressures or EGD. Rather it seeks to exclude the cirrhotic patients who have non-clinically significant portal hypertension (HVPG<12 mmHg) and are not expected to have clinically significant esophageal varices, and therefore, do not need to undergo SOC EGD screening. This biomarkers screening does not seek to establish either an exact numerical value for HVPG or a direct size correlation value for varices, but rather a cut-off value to safely and effectively triage clinical care and procedures, safeguarding the health of the patient while saving valuable clinical resources.

Similarly, in this Example, low values of each individual biomarkers correspond to non-clinically significant esophageal varices (0-5 mm as measured by EGD), while high values of these biomarkers correspond to clinically significant esophageal varices (>5 mm) that would require an EGD for diagnostic and therapeutic interventions. In this example, a large cohort of cirrhotic patients, including ~50% of cirrhotic patients with clinically significant esophageal varices is analyzed and a validation cohort to confirm the findings in a SOC screening EGD is performed. More importantly, a larger cohort, while using all the six identified biomarkers allows a more precise prediction of clinically significant esophageal varices (>5 mm).

A blood test for clinically significant esophageal varices can be effective in all patients, including those unsuitable (e.g., patients with obesity, ascites, congestive heart failure and extrahepatic cholestasis) for other experimental measurements (Liver Stiffness, Spleen Stiffness). The test presented in this example has a similar accuracy in predicting HVPG (with clinically significant esophageal varices) to LS or SS and it can become more accurate with a larger cohort and the more physiologically delineated values of variceal measurements encountered by EGD. Thus, a test based on blood biomarkers could be developed to be more accessible worldwide due to low costs and ease of execution. Certainly if its predictive value for patients with clinically significant esophageal varices as present SOC, correlates with its predictive value for HPVG, and the blood test is executable in all cirrhotic patients, then its clinical value is substantial.

In virtually all diseases associated with inflammation, the pattern involves only select cytokines/chemokines. For example, there is a selective and specific increase in some cytokines/chemokines in the following diseases: i) Inflammatory Bowel Diseases: elevated serum TNFα plays an important role in the pathogenesis of IBD. Therefore, a chimeric monoclonal anti-TNF antibody (infliximab) is used in IBD therapy (55); ii) Cancer-Cachexia is induced by high serum levels of TNFα and IL-6 (56); iii) In Idiopathic Pulmonary Fibrosis: serum CCL18 predicts outcomes (57); iv) Rheumatoid Arthritis: IL-23 serum levels reflect local inflammation associated with this disease (58); and v) Systemic Sclerosis is associated with very high CXCL4 serum levels, whereas the levels of CCL2, CXCL10, CCL5, von Willebrand, and CCL18 did not increase (59).

In the above Example 1, it was reported that only certain specific inflammatory biomarkers (IL-1β, IL-1Rα, Fas-R, VCAM-1, TNF-β and HSP-70) were significantly correlated with HVPG. As documented in many specific non-hepatic inflammatory diseases (55-59), the selectivity of these biomarkers is indicated by the fact that 29 other inflammatory biomarkers were not significantly correlated with HVPG. The aim of this example is to assess whether these biomarkers can identify cirrhotic patients that have non-clinically significant varices. The studies provided in this example suggest that the same biomarkers correlate with clinically significant esophageal varices, as well. Therefore, the validation of a cut-off biomarker(s) value(s) allows excluding cirrhotic patients that have non-clinically significant esophageal varices (0-5 mm) from the SOC EGD screening for esophageal varices.

Methods and Materials

The six specific inflammatory biomarkers predicted non-clinically significant portal hypertension HVPG<12 mmHg are also able to exclude the presence of clinically significant esophageal varices (>5 mm) in cirrhotic patients (2), thus, prevent such patients from undergoing standard of care (SOC) screening by EGD. The ability to also predict non-clinically significant esophageal varices with a blood test revolutionizes clinical management of patients with cirrhosis, as well as aid in the design and performance of clinical research into the complications of cirrhosis (1; 2).

In this example, clinical studies on the sensitivity and specificity of the biomarkers in excluding clinically significant esophageal varices are conducted. The materials required for successful clinical studies include: i) a large cohort of eligible subjects (>700 cirrhotic patients are followed at UCSD and the VASDHS Liver Clinics and >400 subjects undergo EGD for screening esophageal varices as SOC each year); and ii) state-of-the-art endoscopy and laboratory facilities to analyze the inflammatory biomarkers (the primary end-point). These studies suggest an inexpensive laboratory test that could become an innovative standard of care for these cirrhotic patients.

Predictive values of the serum biomarkers IL-1β, IL-1Rα, Fas-R, VCAM-1, TNF-β and HSP-70 are determined for the absence of clinically significant esophageal varices (>5 mm) in cirrhosis. The inclusion criteria for cirrhotic patients are: i) all cirrhotic patients of any etiology undergoing SOC screening for esophageal varices by EGD; and ii) 21-80 years of age. Exclusion criteria are those established by the SOC criteria for EGD screening of esophageal varices (54).

Eligible cirrhotic subjects undergo SOC surveillance by EGD. Following AASLD recommendations, SOC EGD is performed once the diagnosis of cirrhosis is established (4; 49). In patients with compensated cirrhosis who have no varices on screening endoscopy, the EGD is repeated in 2 years (4; 54). In those who have small varices (1-5 mm), the EGD is repeated in 2 years (4; 54). In the presence of decompensated cirrhosis, EGD is repeated at yearly intervals (49; 50). The AASLD Guidelines recommends that the classification be in 2 grades (small and large) (54), by quantitative size with a cut-off diameter of 5 mm (variceal size is measured with a calibrated catheter tip).

The inclusion criteria for control patients are an age-matched control group consisting of 200 healthy individuals without liver disease (as determined by medical history; physical examination; clinical laboratory tests (the same described for cirrhotic patients) and US, CT or MRI liver imaging studies in the preceding 12 months). These control patients are obtained from the UCSD and VASDHS Preventive Health Care Clinics.

All subjects have 10 ml of blood drawn for analysis of the biomarkers and additional SOC clinical laboratory tests (before the EGD for cirrhotic subjects and during their Clinic Visit for healthy control subjects) after signing the Informed Consent. The clinical laboratory tests include CBC with differential and platelets; chemistry panel; liver panel; INR; lipid panel; CRP and HgbA1c. Child-Pugh and MELD scores will be calculated.

Sample Size: Power analysis is performed based on the biomarkers of portal hypertension. The most stringent statistical analysis allows only 1 biomarker per 10 subjects in the smaller occurring subset (clinically significant or non-clinically significant esophageal varices. The power analysis for biomarkers included the following parameters: in order to utilize all six (6) biomarkers, the study sample size is calculated to be 200 subjects in the training set and 200 subjects in the validation set (with an expected an smaller subset of 70-100 of the subjects having clinically significant varices at each site from the 2013 data analysis) ($\alpha$ error: 5% and $\beta$ error: 20%). Thus, if at least 70 subjects are enrolling in the smaller subset at each site, all six (6) biomarkers are able to be used. Esophageal varices' size is measured according to the AASLD Guidelines written by Dr. Garcia-Tsao (54).

An intention-to-diagnose analysis is conducted in patients who undergo SOC surveillance by EGD. The exploratory correlations are assessed with Pearson's correlation coefficient with 95% confidence intervals. Multiple linear regression analysis and logistic regression analysis are then used to test for predictive values of clinically significant varices (>5 mm) The significance level is fixed at $\alpha=5\%$ for all tests. All analyses are performed using the Analyse-it program.

Distribution analysis is performed for all the variables by measuring skewness and kurtosis. Variables that do not have a normal distribution, judging by a skewness >0.5 are log transformed. All variables are analyzed by a two-sided t-test or chi-square test. Univariate logistic regression is run for esophageal varices </=5 mm or esophageal varices >5 mm. The variables that are most significant are submitted to multivariate logistic regression with backward elimination of variables that do not add to the model. The variables that remain are combined by logistic regression to a synthetic composite. ROC curves are produced for the variables and the composite (area; asymptotic sigma P value; and 95% CI will be determined).

A scatter plot is drawn and a cut-off point is selected where probability of esophageal varices >5 mm based on a natural break in the scatter plot. The group below the cut-off point is compared to actual esophageal varices </=5 mm. The sensitivity, specificity, Positive Predictive Value and Negative Predictive Value are computed for actual esophageal varices cut-off at 5 mm. The cut-off at 5 mm means that if the equation predicts esophageal varices is </=5 mm, then it actually is </=5 mm for a given % of the patients (Negative Predictive Value). The Sensitivity, Positive Predictive Value and Specificity for esophageal varices <=5 mm or >5 mm are determined as previously reported (See Example 1). The identified biomarkers are used to determine categories (esophageal varices >5 mm or not) but are not used for continuous measurements since this is unnecessary for this objective.

De-identified blood samples are analyzed in quadruplicates (to assess intra-assay reproducibility) for the six biomarkers as previously described (See Example 1). A multiplex peptide detection system (Milipore) is utilized according to the manufacturer's protocol to determine IL-1β, IL-1Rα, Fas-R, VCAM-1, TNF-β and HSP-70. Values are calculated from individual pixels using the MAGPIX analysis xPonent software and Q-View Imager system, respectively. Intrapatient variability in the levels of these biomarkers is analyzed. Individuals performing the laboratory tests are kept blinded to the subjects' demographics, clinical, and EGD data.

False Negative: In cirrhosis due to genetic hemochromatosis (GH) there are low levels of liver inflammation. Because GH is a rare cause of cirrhosis (<1% in the Transplantation List since phlebotomies prevent development of cirrhosis) this is potentially a minor issue. Further, GH may have comparable levels of the biomarkers to other cirrhotic etiologies with clinically significant esophageal varices. The identification of false negatives at this stage of test development is valuable for future clinical applications.

False Positive: other organ inflammatory diseases may induce a false positive prediction of clinically significant varices. This is not a concern for the development of a biomarkers' test since these patients undergo an EGD needed following the current AASLD Guidelines. The challenge of false positives to this screening while not desirable, do not impact the well-being of the patient as the test is simply unable to limit their EGD SOC procedure, but does not put them at risk. The main objective of these biomarkers is to safely rule out as many patients with non-clinically significant esophageal varices (0-5 mm) as possible, and while these false positive clinical conditions might affect the overall accuracy of the screening, they do not put cirrhotic patients' at risk and are still an improvement in the quality of care that is presently available.

References

1. Bosch J, Abraldes J G, Berzigotti A, Garcia-Pagan J C. (2008). Portal hypertension and gastrointestinal bleeding. Semin Liver Dis. 28(1):3-25. PMID 18293274
2. Report 04-5491. Executive Summary. Action Plan for Liver Disease Research. U.S. Department of Health and Human Services: (2004) NIH. pp. 1-6.
3. Groszmann R J, Bosch J, Grace N, Conn H O, Garcia-Tsao G, Navasa M, et al. Hemodynamic events in a prospective randomized trial of propranolol vs placebo in the prevention of the first variceal hemorrhage. Gastroenterology 1990; 99:1401-1407
4. DeFranchis R. Updating consensus in portal hypertension: Report of the Baveno III consensus workshop on definitions, methodology and therapeutic strategies in portal hypertension. J Hepatol
5. Garcia-Tsao G, Groszmann R J, Fisher R L, Conn H O, Atterbury C E, Glickman M. Portal pressure, presence of gastroesophageal varices and variceal bleeding. Hepatology 1985; 5:419-424.
6. Feu F, Garcia-Pagan J C, Bosch J, Luca A, Teres J, Escorsell A, Rodes J. Relation between portal pressure response to pharmacotherapy and risk of recurrent variceal haemorrhage in patients with cirrhosis. Lancet 1995; 346:1056-1059.
7. D'Amico G, Garcia-Pagan J C, Luca A, Bosch J. HVPG reduction and prevention of variceal bleeding in cirrhosis. A systematic review. Gastroenterology 2006; 131:1624.
8. Abraldes J G, Tarantino I, Turnes J, Garcia-Pagan J C, Rodes J, Bosch J. Hemodynamic response to pharmacological treatment of portal hypertension and long-term prognosis of cirrhosis. Hepatology 2003; 37:902-908.
9. Castera L, Pinzani M, Bosch J. (2012). Non invasive evaluation of portal hypertension using transient elastography. J Hepatol. 56(3):696-703. PMID: 21767510
10. Bellot P, García-Pagán J C, Francés R, Abraldes J G, Navasa M, Pérez-Mateo M, Such J, Bosch J. (2010). Bacterial DNA translocation is associated with systemic circulatory abnormalities and intrahepatic endothelial dysfunction in patients with cirrhosis. Hepatology. 52(6): 2044-52. PMID: 20979050
11. Chung R and Podolsky D. (2005). Cirrhosis and its Complications. In: Harrison's Principles of Internal Medicine, New York: McGraw-Hill, pp. 1754-1767.
12. Francés R, Rodriguez E, Muñoz C, Zapater P, De la M L, Ndongo M, Pérez-Mateo M, Such J. (2005). Intracellular cytokine expression in peritoneal monocyte/macrophages obtained from patients with cirrhosis and presence of bacterial DNA. Eur J Gastroenterol Hepatol. 17(1):45-51. PMID: 15647640
13. Francés R, Zapater P, González-Navajas J M, Muñoz C, Caño R, Moreu R, Pascual S, Bellot P, Pérez-Mateo M, Such J. (2008). Bacterial DNA in patients with cirrhosis and noninfected ascites mimics the soluble immune response established in patients with spontaneous bacterial peritonitis. Hepatology. 47(3):978-85. PMID: 18306221
14. Chojkier M. (1998). Regulation of collagen gene expression. In: Strain A, Diehl A, editors. Liver growth and repair. London: Chapman & Hall. pp. 430-450.
15. Picchiotti R, Mingazzini P L, Scucchi L, Bressan M, Di Stefano D, Donnetti M, Feroci L. (1994). Correlations between sinusoidal pressure and liver morphology in cirrhosis. J Hepatol. 20(3):364-9. PMID: 8014448
16. Groszmann R J, Garcia-Tsao G, Bosch J, Grace N D, Burroughs A K, Planas R, Escorsell A, Garcia-Pagan J C, Patch D, Matloff D S, Gao H, Makuch R; Portal Hypertension Collaborative Group. (2005). Beta-blockers to prevent gastroesophageal varices in patients with cirrhosis. N Engl J Med. 353(21):2254-61. PMID: 16306522
17. Lebrec D., Nouel O, Bernuau J, Rueff B, and Benhamou J P. Portal hypertension in fulminant viral hepatitis. Gut, 21, 962-964, 1980.
18. Valla D, Flejou J F, Lebrec D, Bernuau J, Rueff B, Salzmann J L, Benhamou J P. (1989). Portal hypertension and ascites in acute hepatitis: clinical, hemodynamic and histological correlations. Hepatology. 10(4):482-7. PMID: 2777210
19. Reynolds T B, Hidemura R, Michel H and Peters R. Portal Hypertension Without Cirrhosis in Alcoholic Liver Disease .Ann Intern Med. 1 Mar. 1969; 70 (3):497-506
20. Boraschi D, Tagliabue A. (2006). The interleukin-1 receptor family. Vitam Horm. 74:229-54. PMID: 17027517
21. Elkon K B. (2007). IL-1alpha responds to necrotic cell death. Nat Med. 13(7):778-80. PMID: 17618263
22. D'Amico G, Garcia-Tsao G, Pagliaro L. Natural history and prognostic indicators of survival in cirrhosis. A systematic review of 118 studies. J Hepatol 2006; 44:217-231.
23. Villanueva C, Minana J, Ortiz J, Gallego A, Soriano G, Torras X, Sainz S, Boadas J, Cusso X, Guarner C, Balanzo J. Endoscopic ligation compared with combined treatment with nadolol and isosorbide mononitrate to prevent recurrent variceal bleeding. N Engl J Med 2001; 345:647-655.

24. Franchi L, Eigenbrod T, Muñoz-Planillo R, Nuñez G. (2009). The inflammasome: a caspase-1-activation platform that regulates immune responses and disease pathogenesis. Nat Immunol. 10(3):241-7. PMID: 19221555
25. Lebrec D, De Fleury P, Rueff B, Nahum H, Benhamou J P. Portal hypertension, size of esophageal varices, and risk of gastrointestinal bleeding in alcoholic cirrhosis. Gastroenterology 1980; 79:1139-1144.
26. DeFranchis R, Pascal J P, Burroughs A K, Henderson J M, Fleig W, Groszmann R J, Bosch J, Sauerbruch T, Soederlund C. Definitions, methodology and therapeutic strategies in portal hypertension. A Consensus Development Workshop. J Hepatol 1992; 15:256-261.
27. Haybaeck J, Zeller N, Wolf M J, Weber A, Wagner U, Kurrer M O, Bremer J, Iezzi G, Graf R, Clavien P A, Thimme R, Blum H, Nedospasov S A, Zatloukal K, Ramzan M, Ciesek S, Pietschmann T, Marche P N, Karin M, Kopf M, Browning J L, Aguzzi A, Heikenwalder M. (2009). A lymphotoxin-driven pathway to hepatocellular carcinoma. Cancer Cell. 16(4):295-308. PMID: 19800575
28. Izquierdo J M, Majós N, Bonnal S, Martínez C, Castelo R, Guigó R, Bilbao D, Valcárcel J. (2005). Regulation of Fas alternative splicing by antagonistic effects of TIA-1 and PTB on exon definition. Mol Cell. 19(4):475-84. PMID: 16109372
29. Wajant H. (2002). The Fas signaling pathway: more than a paradigm. Science. 296(5573):1635-6. PMID: 12040174
30. Carluccio M A, Ancora M A, Massaro M, Carluccio M, Scoditti E, Distante A, Storelli C, De Caterina R. (2007). Homocysteine induces VCAM-1 gene expression through NF-kappaB and NAD(P)H oxidase activation: protective role of Mediterranean diet polyphenolic antioxidants. Am J Physiol Heart Circ Physiol. 293(4):H2344-54. PMID: 17586618
31. Oertli B, Beck-Schimmer B, Fan X, Wüthrich R P. (1998). Mechanisms of hyaluronan-induced up-regulation of ICAM-1 and VCAM-1 expression by murine kidney tubular epithelial cells: hyaluronan triggers cell adhesion molecule expression through a mechanism involving activation of nuclear factor-kappa B and activating protein-1. J Immunol. 161(7):3431-7. PMID: 9759861
32. Pueyo M E, Gonzalez W, Nicoletti A, Savoie F, Arnal J F, Michel J B. (2000). Angiotensin II stimulates endothelial vascular cell adhesion molecule-1 via nuclear factor-kappaB activation induced by intracellular oxidative stress. Arterioscler Thromb Vasc Biol. 20(3):645-51. PMID: 10712386
33. Abdelmoneim S S, Talwalkar J, Sethi S, Kamath P, Fathalla M M, Kipp B R, Campion M B, Clayton A C, Halling K C, Shah V H. (2010). A prospective pilot study of circulating endothelial cells as a potential new biomarker in portal hypertension. Liver Int. 30(2):191-7. PMID: 19840257
34. Bataller R, Gäbele E, Parsons C J, Morris T, Yang L, Schoonhoven R, Brenner D A, Rippe R A. (2005). Systemic infusion of angiotensin II exacerbates liver fibrosis in bile duct-ligated rats. Hepatology. 2005 May; 41(5): 1046-55. PMID: 15841463
35. Bosy-Westphal A, Ruschmeyer M, Czech N, Oehler G, Hinrichsen H, Plauth M, Lotterer E, Fleig W, Müller M J. (2003). Determinants of hyperhomocysteinemia in patients with chronic liver disease and after orthotopic liver transplantation. Am J Clin Nutr. 77(5):1269-77. PMID: 12716682
36. Engström-Laurent A, Lööf L, Nyberg A, Schröder T. (1985). Increased serum levels of hyaluronate in liver disease. Hepatology. 5(4):638-42. PMID: 4018736
37. Torres L, García-Trevijano E R, Rodríguez J A, Carretero M V, Bustos M, Fernández E, Eguinoa E, Mato J M, Avila M A. (1999). Induction of TIMP-1 expression in rat hepatic stellate cells and hepatocytes: a new role for homocysteine in liver fibrosis. Biochim Biophys Acta. 1455(1):12-22. PMID: 10524225
38. Wang X Y, Kazim L, Repasky E A, Subjeck J R. (2001). Characterization of heat shock protein 110 and glucose-regulated protein 170 as cancer vaccines and the effect of fever-range hyperthermia on vaccine activity. J Immunol. 166(1):490-7. PMID: 11123328.
39. Xue H, Slavov D, Wischmeyer P E. (2012). Glutamine-mediated dual regulation of heat shock transcription factor-1 activation and expression. J Biol Chem. 287(48): 40400-13. PMID: 23055521
40. Vizzutti F, Arena U, Romanelli R G, Rega L, Foschi M, Colagrande S, Petrarca A, Moscarella S, Belli G, Zignego A L, Marra F, Laffi G, Pinzani M. (2007). Liver stiffness measurement predicts severe portal hypertension in patients with HCV-related cirrhosis. Hepatology. 45(5): 1290-7. PMID: 17464971
41. Castéra L, Foucher J, Bernard P H, Carvalho F, Allaix D, Merrouche W, Couzigou P, de Lédinghen V. (2010). Pitfalls of liver stiffness measurement: a 5-year prospective study of 13,369 examinations. Hepatology. 51(3): 828-35. PMID: 20063276
42. Sandrin L, Fourquet B, Hasquenoph J M, Yon S, Fournier C, Mal F, Christidis C, Ziol M, Poulet B, Kazemi F, Beaugrand M, Palau R. (2003). Transient elastography: a new noninvasive method for assessment of hepatic fibrosis. Ultrasound Med Biol. 29(12):1705-13. PMID: 14698338
43. Berzigotti A, De Gottardi A, Vukotic R, Siramolpiwat S, Abraldes J G, García-Pagan J C, Bosch J. (2013). Effect of meal ingestion on liver stiffness in patients with cirrhosis and portal hypertension. PLoS One. 8(3):e58742. PMID: 23520531
44. Berzigotti A, Seijo S, Arena U, Abraldes J G, Vizzutti F, García-Pagán J C, Pinzani M, Bosch J. (2013). Elastography, spleen size, and platelet count identify portal hypertension in patients with compensated cirrhosis. Gastroenterology. 144(1):102-111.e1. PMID: 23058320
45. Berzigotti A, Garcia-Tsao G, Bosch J, Grace N D, Burroughs A K, Morillas R, Escorsell A, Garcia-Pagan J C, Patch D, Matloff D S, Groszmann R J; Portal Hypertension Collaborative Group. (2011). Obesity is an independent risk factor for clinical decompensation in patients with cirrhosis. Hepatology. 54(2):555-61. PMID: 21567436.
46. Colecchia A, Montrone L, Scaioli E, Bacchi-Reggiani M L, Colli A, Casazza G, Schiumerini R, Turco L, Di Biase A R, Mazzella G, Marzi L, Arena U, Pinzani M, Festi D. Measurement of spleen stiffness to evaluate portal hypertension and the presence of esophageal varices in patients with HCV-related cirrhosis. Gastroenterology. 2012; 143: 646-54.
47. Sharma P, Kirnake V, Tyagi P, Bansal N, Singla V, Kumar A, Arora A. Spleen Stiffness in Patients With Cirrhosis in Predicting Esophageal Varices. Am J Gastroenterol 2013; 108:1101-1107;
48. World Health Organization. (2002) The World Health report 2002: reducing risks, promoting healthy life. Geneva, Switzerland: WHO; pp. 1-230.

49. Grace N D, Groszmann R J, Garcia-Tsao G, Burroughs A K, Pagliaro L, Makuch R W, Bosch J, Stiegmann G V, Henderson J M, DeFranchis R, Wagner J L, Conn H O, Rodes J. Portal hypertension and variceal bleeding: an AASLD single topic symposium. Hepatology 1998; 28:868-880.

50. D'Amico G, Garcia-Tsao G, Cales P, Escorsell A, Nevens F, Cestari R, Caletti G, Zoli M. Diagnosis of portal hypertension: how and when. In: DeFranchis R. ed. Portal Hypertension III. Proceedings of the Third Baveno International Consensus Workshop on Definitions, Methodology and Therapeutic Strategies. Oxford: Blackwell Science, 2001: 36-64.

51. Eisen G M, Eliakim R, Zaman A, Schwartz J, Faigel D, Rondonotti E, Villa F, Weizman E, Yassin K, DeFranchis R. The accuracy of PillCam ESO capsule endoscopy versus conventional upper endoscopy for the diagnosis of esophageal varices: a prospective three-center pilot study. Endoscopy 2006; 38: 31-35.

52. Lapalus M G, Dumortier J, Fumex F, Roman S, Lot M, Prost B, Mion F, Ponchon T. Esophageal capsule endoscopy versus esophagogastroduodenoscopy for evaluating portal hypertension: a prospective comparative study of performance and tolerance. Endoscopy 2006; 38: 36-41.

53. Buck M, Garcia-Tsao G, Groszmann R J, Stalling C, Grace N D, Burroughs A K, Patch D, Matloff D S, Clopton P, Chojkier M. Novel inflammatory biomarkers of portal pressure in compensated cirrhotic patients. Hepatology. 2013 Oct. 1 [Epub ahead of print] PMID: 24115225

54. Garcia-Tsao G, Sanyal A J, Grace N D, Carey W. Prevention and management of gastroesophageal varices and variceal hemorrhage in cirrhosis. Hepatology 2007; 46:922-938 and Am J Gastroenterol 2007; 102:2086-2102.

55. Bouguen G, Levesque B G, Feagan B G, Kavanaugh A, Peyrin-Biroulet L, Colombel J F, Hanauer S B, Sandborn W J. Treat to Target: A Proposed New Paradigm for the Management of Crohn's Disease. Clin Gastroenterol Hepatol. 2013 Sep. 10. pii: S1542-3565(13)01301-3. doi: 10.1016/j.cgh.2013.09.006. [Epub ahead of print].

56. Ramamoorthy S, Donohue M, Buck M. Decreased Jun-D and myogenin expression in muscle wasting of human cachexia. Am J Physiol Endocrinol Metab. 2009 August; 297(2):E392-401. doi: 10.1152/ajpendo.90529.2008. Epub 2009 May 26. PMID: 19470832.

57. Prasse A, Probst C, Bargagli E, Zissel G, Toews G B, Flaherty K R, Olschewski M, Rottoli P, Müller-Quernheim J. Serum CC-chemokine ligand 18 concentration predicts outcome in idiopathic pulmonary fibrosis. Am J Respir Crit Care Med. 2009 Apr. 15; 179(8):717-23. doi: 10.1164/rccm.200808-12010C. Epub 2009 Jan. 29. PMID: 19179488.

58. Kageyama Y, Ichikawa T, Nagafusa T, Torikai E, Shimazu M, Nagano A. Etanercept reduces the serum levels of interleukin-23 and macrophage inflammatory protein-3 alpha in patients with rheumatoid arthritis. Rheumatol Int. 2007 December; 28(2):137-43. Epub 2007 Jul. 10. PMID: 17619881.

59. Lenny van Bon, Alsya J. Affandi, Jasper Broen, et al. Proteome-wide Analysis and CXCL4 as a Biomarker in Systemic Sclerosis N Engl J Med 2014; 370:433-443 Jan. 30, 2014 DOI: 10.1056/NEJMoa1114576.

What is claimed is:

1. A method of treating a patient with cirrhosis, comprising:
   a) determining, based at least in part on expression levels of five or more biomarkers in a biological sample of the patient, whether a hepatic vein pressure gradient (HVPG) in the patient is less than 12 mmHg, wherein the biomarkers are selected from IL-1β, IL-1Rα, Fas-R, VCAM-1, TNF-β, HSP-70, IL-18, TLR9, lymphotoxin-β, glutamine, glutamine synthase, HSP-27, HSP-60, HSP-110, grp170, hyaluronan, homeocysteine, and angiotensin-II; and
   b) performing esophagogastricduodenoscopy (EGD) on the patient to treat esophageal varices when the HVPG in the patient is determined not to be less than 12 mmHg.

2. The method of claim 1, wherein said biological sample is whole blood, plasma, or serum.

3. The method of claim 1, wherein determining whether the HVPG in the patient is less than 12 mmHg is based, at least in part, on the expression levels of at least six biomarkers: IL-1β, IL-1Rα, Fas-R, VCAM-1, TNF-β and HSP-70.

4. The method of claim 1, wherein determining whether the HVPG in the patient is less than 12 mmHg is based, at least in part, on demographic and clinical laboratory parameters selected from the group consisting of age, model for end-stage liver diseases (MELD), Child-Pugh Score (CPS), platelets, alanine aminotransferase (ALT), aspartate aminotransferase (AST), and at-risk alcohol use.

5. The method of claim 1, wherein the determining step determines the HVPG in the patient is less than 12 mmHg with at least 86% accuracy.

6. The method of claim 3, wherein determining whether the HVPG in the patient is less than 12 mmHg is based, at least in part, on correlating the expression levels of the at least six biomarkers to HVPG<vs HVPG=/>12mmHg as follows: IL-1β (5.9+/−1.2 vs 22.9+/−1.2 pg/ml), IL-1Rα (53.1+/−12.0 vs 158.2+/−101.3 pg/ml), Fas-R (8.7+/−0.2 vs 9.3+/−0.5 ng/ml), VCAM-1 (1.1+/−0.09 vs 1.4+/−0.01; ng/ml), TNF-β (0.4+/−0.04 vs 0.6+/−0.06 ng/ml) and HSP-70 (42.6+/−1.2 vs 81.9+/−15.3 ng/ml).

7. The method of claim 1, wherein the determining step determines whether the HVPG in the patient is less than 12 mmHg non-invasively.

8. The method of claim 1, wherein said method is used in conjunction with established demographic and clinical laboratory parameters selected from the group consisting of age, model for end-stage liver diseases (MELD), Child-Pugh Score (CPS), platelets, alanine aminotransferase (ALT), aspartate aminotransferase (AST), and at-risk alcohol use.

9. The method of claim 4, wherein persons with non-clinically significant HVPG and esophageal varices are excluded from undergoing standard of care EGD.

10. The method of claim 1, further comprising determining that the patient has severe portal hypertension at levels associated with variceal bleeding and ascites when the HVPG in the patient is determined not to be less than 12 mmHg.

* * * * *